United States Patent
Poloso et al.

(10) Patent No.: US 10,117,877 B2
(45) Date of Patent: *Nov. 6, 2018

(54) METHODS FOR FAT REDUCTION

(71) Applicant: ALLERGAN, INC., Irvine, CA (US)

(72) Inventors: Neil J. Poloso, Lake Forest, CA (US); Jenny Wang, Irvine, CA (US); David F. Woodward, Lake Forest, CA (US); Robert M. Burk, Laguna Beach, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/721,303

(22) Filed: Sep. 29, 2017

(65) Prior Publication Data
US 2018/0071308 A1    Mar. 15, 2018

Related U.S. Application Data

(63) Continuation of application No. 15/143,223, filed on Apr. 29, 2016, now Pat. No. 9,795,615.

(60) Provisional application No. 62/154,926, filed on Apr. 30, 2015.

(51) Int. Cl.
| | |
|---|---|
| *A61K 31/559* | (2006.01) |
| *A61Q 19/06* | (2006.01) |
| *A61K 8/49* | (2006.01) |
| *A61Q 7/02* | (2006.01) |

(52) U.S. Cl.
CPC .......... *A61K 31/559* (2013.01); *A61K 8/4986* (2013.01); *A61Q 19/06* (2013.01); *H05K 999/99* (2013.01); *A61Q 7/02* (2013.01)

(58) Field of Classification Search
CPC ...... A61K 31/559; A61K 8/4986; A61Q 7/02; A61Q 19/06
See application file for complete search history.

(56) References Cited

U.S. PATENT DOCUMENTS

| | | | |
|---|---|---|---|
| 6,248,773 B1 | 6/2001 | Burk | |
| 6,602,900 B2 * | 8/2003 | Burk | A61K 31/381 514/365 |
| 7,666,912 B2 | 2/2010 | Grosskreutz et al. | |
| 9,795,615 B2 | 10/2017 | Poloso et al. | |
| 2012/0270941 A1 | 10/2012 | Rethore | |
| 2014/0155488 A1 | 6/2014 | Warner et al. | |
| 2014/0275272 A1 | 9/2014 | Poloso et al. | |

FOREIGN PATENT DOCUMENTS

| | | | | |
|---|---|---|---|---|
| WO | 1996-036599 | 11/1996 | | |
| WO | 1997-031895 | 9/1997 | | |
| WO | 2007111806 | 10/2007 | | |
| WO | 2008070402 | 6/2008 | | |
| WO | WO2011109384 | 4/2012 | | |
| WO | WO 2014169075 A1 * | 10/2014 | ......... | A61K 31/5575 |
| WO | 2014-183045 | 11/2014 | | |
| WO | 2015-200425 | 12/2015 | | |

OTHER PUBLICATIONS

A.G.Messenger, Minoxidil: mechanism of action on hair growth, British Journal of Dermatology, 2004, 186-194, 150.
Author Unknown, Ferriman Gallwey Evaluation of Hirsutism and its Pattern, Hirsutism.com, pp. 1-3, retrieved on Mar. 23, 2015 from http://www.hirsutism.com/hirsutism-biology/ferriman-gallwey-score.shtml.
Bume-Peytavy, U., et al., Hair Growth & Disorders, Hair Growth & Disorders, 2008, 1-571, N/A, Springer.
Caruso, MK, et al., Topical fat reduction from the waist, Diabetes, Obesity and Metabolism, 2007, 300-303, 9.
Choi, Hee Young et al, In Vitro Study of Antiadipogenic Profile of Latanoprost, Travoprost, Bimatoprost, and Tafluprost in Human Orbital Preadiopocytes, Journal of Ocular Pharmacology and Therapeutics, 2012, 146-152, 28(2).
Colombe, Laurent et al, Prostaglandin metabolism in human hair follicle, Experimental Dermatology, May 16, 2007, 762-769, 16, US.
Conway, JM, et al., A New Approach for the Estimation of Body Composition: Infrared Interactance, The American Journal of Clinical Nutrition, 1984, 1123-1130, 40.
Cross, LC, Rules for the Nomenclature of Organic Chemistry Section E: Sterochemistry, Pure & Appl. Chem., 1976, 11-30, 45.
David Ferriman, Clinical assessment of body hair growth in women, Journal of Clinical Endocrinology & Metabolism, 1961, 1440-1447.
Food & Drug Administration-Center for Drug Evaluation & Research, Guidance for Industry: Estimating the Maximum Safe Starting Dose in Initial Clinical Trails for Therapeutics in Adult Healthy Volunteers, Jul. 2055—Pharmacology & Toxicology, 2005, 1-30.
Goodman, Neil F., AACE Hyperandrogenism Guidelines, Endocrine Practice, 2001, 120-134, 7 (2).
Greenway, FL, et al., Topical Fat Reduction, Obesity Research, 1995, 561S-568S, 3 (Suppl 4).
Guillory, J. Keith, Generation of Polymorphs, Hydrates, Solvates, and Amorphous Solids, Chap. 5, 183-226, 1999.
International Search Report & Written Opinion dated Jul. 4, 2016 for PCT/US16/30251 filed Apr. 29, 2016 on Allergan, Inc.
International Search Report & Written Opinion dated Aug. 29, 2014 for PCT/US14/33558 filed Apr. 9, 2014 in the name of Allergan, Inc.
Johnstone, Murray et al, Prostaglandin-Induced Hair Growth, Survey of Ophthalmology, Aug. 2002, S185-S202, 47(Suppl 1).
Johnstone, Murray, Hypertrichosis and Increased Pigmentation of Eyelashes and Adjacent Hair in the Region of the Ipsilateral Eyelids of Patients Treated With Unilateral Topical Latanoprost, American Journal of Ophthalmology, 1997, 544-547, 124(4).
Karzan Khidhir, The prostamide-related glaucoma therapy, bimatoprost, offers a novel approach for treating scalp alopecias, The FASEB Journal, 2013, 557-567, 27.

(Continued)

*Primary Examiner* — Yong L Chu
(74) *Attorney, Agent, or Firm* — Jonathan Bass

(57) ABSTRACT

Disclosed herein are methods, compounds, and compositions for fat reduction, and in particular fat reduction without significant hair growth and/or additional hair growth.

9 Claims, 17 Drawing Sheets

(56) References Cited

OTHER PUBLICATIONS

Latisse, Highlights of Prescribing Information, 2014, pp. 1-12.
Lee, Ping-Yu et al, The Effect of Prostaglandin F2α on intraocular Pressure in Normotensive Human Subjects, Investigative Ophthalmology & Visual Science, Oct. 1988, 1474-1477, 29(10).
Liang, Y. et al, Identification and Pharmacological Characterization of the Prostaglandin FP Receptor and FP Receptor Variant Complexes, Br. J. Pharmacol., 2008, 1079-1093, 154.
Lubura, M., et al., Non-Invasive Quantification of White and Brown Adipose, PLoS One, 2012, 1-8, 7 (5).
Magnetic Resonance Techniques for Fat Quantification in Obesity, retrieved from www.apsipa.org/proceedings_2012/papers/235.pdf on Feb. 20, 2015, pp. 1-10.
McCarey, B.E., et al., Low Incidence of Iris Pigmentation and, Ophthalmology, 2004, 1480-1488, 111, American Academy of Ophthalmology.
McDiarmid, J., et al., Results from a Pooled Analysis of Two European, Randomized Aesth. Plast. Surg., 2014, 849-860, 38.
Ming Li, Minoxidil-Induced Hair Growth is Mediated by Adenosine in Cultured Dermal Papilla Cells: Possible Involvement of Sulfonylurea Receptor 2B as a Target of Minoxidil, Journal of Investigative Dermatology, 2001, 1594-1600, 117.
Plikus, M., et al., Complex Hair Cycle Domain Patterns and Regenerative, Journal of investigative Dermatology, 2008, 1071-1080, 128.
Rittes, P., The Use of Phosphatidylcholine for Correction of Localized Fat Deposits, Aesth. Plast. Surg., 2003, 315-318.
Rolf Holmann, TrichoScan: A Novel Tool for the Analysis of Hair Growth InVivo, Journal of Investigative Dermatology Symposium Porceedings, 2003, 109-115, 8 (1).
Rzany, B., et al., Reduction of unwanted submental fat with ATX-101, British Journal of Dermatology, 2014, 445-453, 170.
Sharif et al., Agonist activity of bimatoprost, travoprost, latanoprost, unoprostone isopropyl ester and other prostaglandin analogs at the cloned human ciliary body FP prostaglandin receptor. J. Ocul Pharmacal Ther. Aug. 2002;18(4):313-24.
Sharif, Najam, Bimatoprost and Its Free Acid Are Prostaglandin FP Receptor Agonists, European Journal of Pharmacology, 2001, 211-213, 432.
Smalls, L.K., Quantitative model of cellulite: three-dimensional skin surface topography, biophysical characterization, and relationship to human perception, Int'l. Journal of Cosmetic Science, 2005, 295, 27.
TrichoScan® Corp., TrichoScan®, 2016, Retrieved from http://trichoscan.com/pages/english/home.php.
Ulrike Blume-Peytavi, Hair Growth Assestment Techniques, Hair Growth and Disorders, 2008, 125-157, Chapter 8.
Westerink, J., et al., Pharmacological and non-pharmacological, Cardiovascular Diabetology, 2011, 13-24, 10.
Wikipedia, entry on Adipose tissue, retrieved on Jan. 28, 2015, pp. 1-9.
Wikipedia, entry on Body fat percentage, retrieved on Feb. 20, 2015, pp. 1-7.
Wikipedia, entry on Brown adipose tissue, retrieved on Feb. 20, 2015, pp. 1-7.
Wikipedia, entry on Obesity, retrieved on Jan. 28, 2015, pp. 1-28.
Wikipedia, entry on Weight loss, retrieved on Jan. 28, 2015, pp. 1-7.
Wikipedia, entry on Wiite adipose tissue, retrieved on Feb. 20, 2015, pp. 1-2.
Woodward, David et al, Recent Progress in Prostaglandin F2α Ethanolamide (Prostamide F2α) Research and Therapeutics, Pharmacological Reviews, Jul. 2013, 1135-1147, 65(4).

\* cited by examiner

METHODS FOR FAT REDUCTION

CROSS-REFERENCE TO RELATED APPLICATIONS

This application is a continuation of U.S. patent application Ser. No. 15/143,223, filed Apr. 29, 2016, now U.S. Pat. No. 9,795,615, which claims the benefit of U.S. provisional patent application 62/154,926 filed on Apr. 30, 2015, which are herein incorporated by reference in their entireties and serve as the basis of a priority and/or benefit claim for the present application.

FIELD

The present disclosure relates generally to methods for fat reduction, and in particular to therapeutic fat reduction and cosmetic fat reduction which are not accompanied by substantial hair growth or additional hair growth at the site of fat reduction.

BACKGROUND

Excess fat in an individual can be undesirable for a number of reasons. In some cases, the excess fat can be aesthetically unpleasing, such as in the case of cellulite, and other externally visible fat deposits such as, for example, fat deposits in the submental (under the chin), abdominal, waist, and thigh regions. In other cases, excess fat can result in obesity, which can be associated with, and increase the likelihood of, a myriad of diseases and conditions such as, for example type 2 diabetes, sleep apnea, heart disease, some types of cancer, osteoarthritis, and others. Consequently, there is a need for cosmetic fat reduction and therapeutic fat reduction.

Many methods for fat reduction generally involve exercise and diet control. However methods of fat reduction by administration of fat-reducing compounds offer advantages such as simplicity, ease of implementation, and an ability to target fat deposits in both systemic (e.g. throughout the whole body of the individual) and localized (e.g. directly to submental fat and/or cellulite deposits) manners. In particular, the compound bimatoprost is one compound which has been shown to reduce body weight (see e.g., US Patent Application Publications 2014/0275272 and US 2014/0308354). However, bimatoprost administration sometimes results in hair growth, an effect exemplified by the marketing of bimatoprost formulations as the product LATISSE®. Such hair growth is not always desirable and may in fact sometimes be undesirable.

Therefore, there is a need for methods of fat reduction which do not result in concomitant hair growth, such as hair growth at the site at which fat reduction is desired. Additionally, there is also a need for a method or treatment in which fat deposits are reduced substantially without the pain and inflammation associated with fat cell freezing, heating, lysing, or otherwise destroying the fat deposits through physical or chemical means.

SUMMARY

Described herein are methods for fat reduction, and in particular methods for fat reduction which do not result in substantial hair growth or additional hair growth at the site of fat reduction.

In one aspect, disclosed herein is a method of reducing body fat in a subject comprising administering to a subject in need thereof an effective amount compound of Formula I, a compound of Formula II, or a mixture thereof:

In another aspect, an effective amount of the compound of formula I is administered.

In another aspect, an effective amount of the compound of formula II is administered.

In another aspect, the compound or mixture of compounds is administered in an amount effective for reducing fat without causing substantial hair growth at the site of fat reduction.

In another aspect, the compound or mixture of compounds is administered in an amount effective for reducing fat without causing additional hair growth at the site of fat reduction.

In another aspect, the compound or mixture of compounds is administered in an amount of about 0.05 mg/kg to about 5 mg/kg.

In another aspect, the compound or mixture of compounds is administered in an amount of about 0.3 mg/kg to about 5 mg/kg.

In another aspect, the compound or mixture of compounds is administered topically, by injection, transdermally, or orally.

In another aspect, the compound or mixture of compounds is administered to at least one of the subject's submental region, thighs, abdomen, or waist.

In another aspect, the compound or mixture of compounds is administered systemically.

In another aspect, the compound or mixture of compounds is administered locally to a fat deposit.

In another aspect, described herein is a pharmaceutical composition for use in reducing fat comprising an effective amount compound of Formula I, a compound of Formula II, or a mixture thereof:

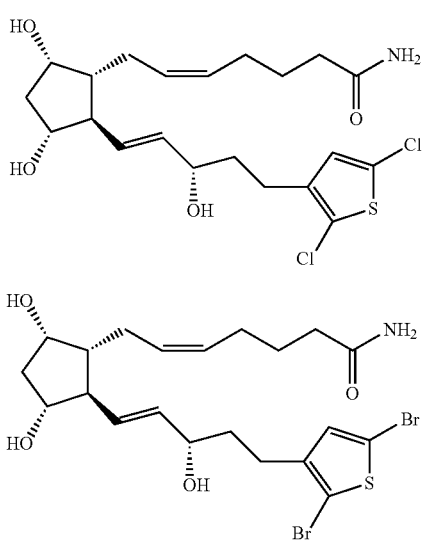

and one or more pharmaceutically acceptable excipients.

In another aspect, the composition comprises an effective amount of the compound of Formula I.

In another aspect, the composition comprises an effective amount of the compound of Formula II.

In another aspect, the composition reduces fat without causing substantial hair growth at the site of fat reduction.

In another aspect, the composition reduces fat without causing additional hair growth at the site of fat reduction.

In another aspect, the composition comprises the compound or mixture of compounds in an amount of about 0.05 mg/kg to about 5 mg/kg.

In another aspect, the composition comprises the compound or mixture of compounds in an amount of about 0.3 mg/kg to about 5 mg/kg.

In another aspect, the composition is suitable to be administered topically, by injection, transdermally, or orally.

In another aspect, the composition is suitable to be administered to at least one of the subject's submental region, thighs, abdomen, or waist.

In another aspect, the composition is suitable to be administered systemically.

In another aspect, the composition is suitable to be administered locally to a fat deposit.

DESCRIPTION OF THE DRAWINGS

FIG. 4A shows the day hair re-growth commenced and FIG. 4B shows day of full hair growth was achieved. These were measured in a masked fashion evaluated by digital photograph.

FIG. 5A shows the graph of male rat weight change and FIG. 5B shows the graph of female rat weight change. After day 183, animals were allowed to recover without drug administration up to 30 days.

DETAILED DESCRIPTION

Figure 1A:
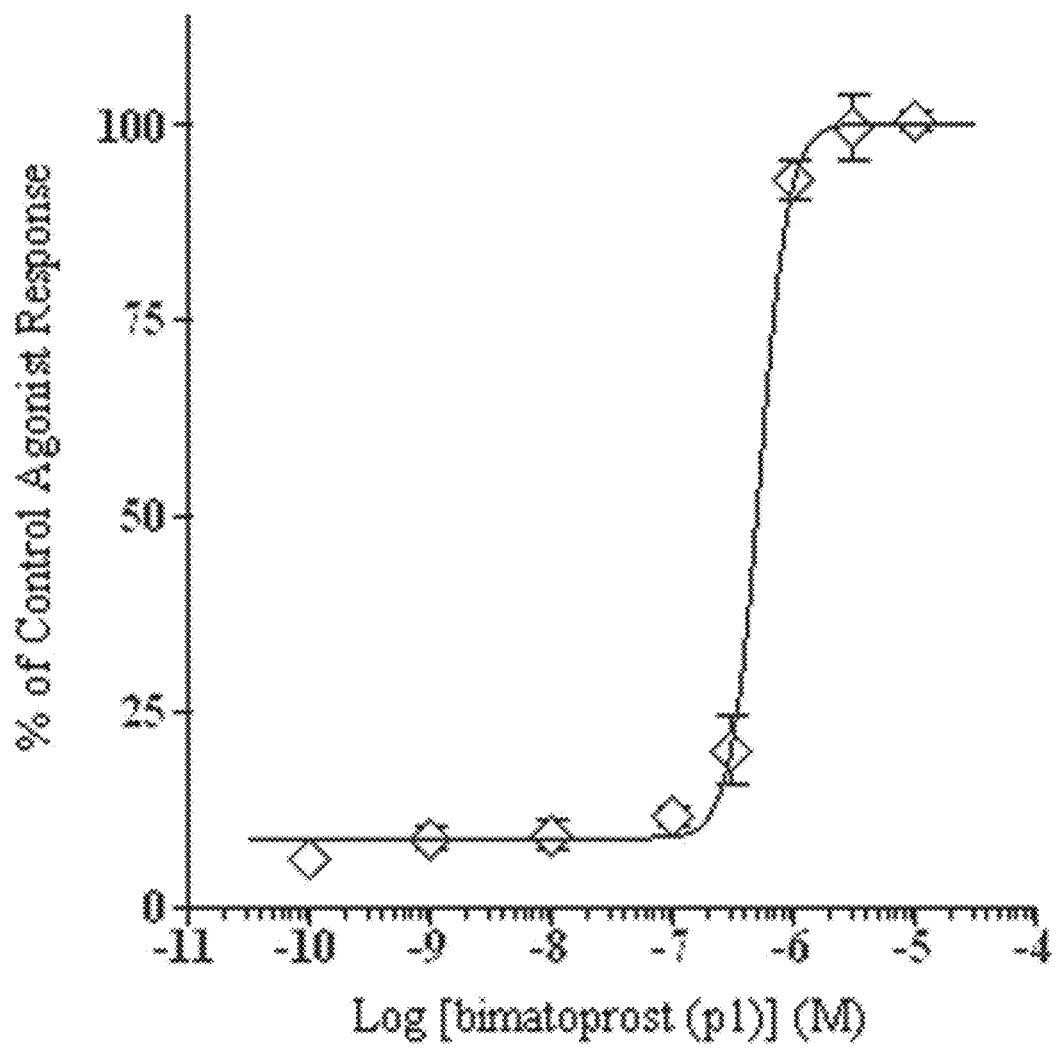
FIG. 1A, FIG. 1B, FIG. 1C, and FIG. 1D show the results of agonist response in the triplicate impedance assays (FIGS. 1A, 1B, and 1C) and signature trace of the top dose (FIG. 1D) with human dermal papilla cells in an in vitro cell dielectric spectroscopy assay with bimatoprost.
Figure 1B:
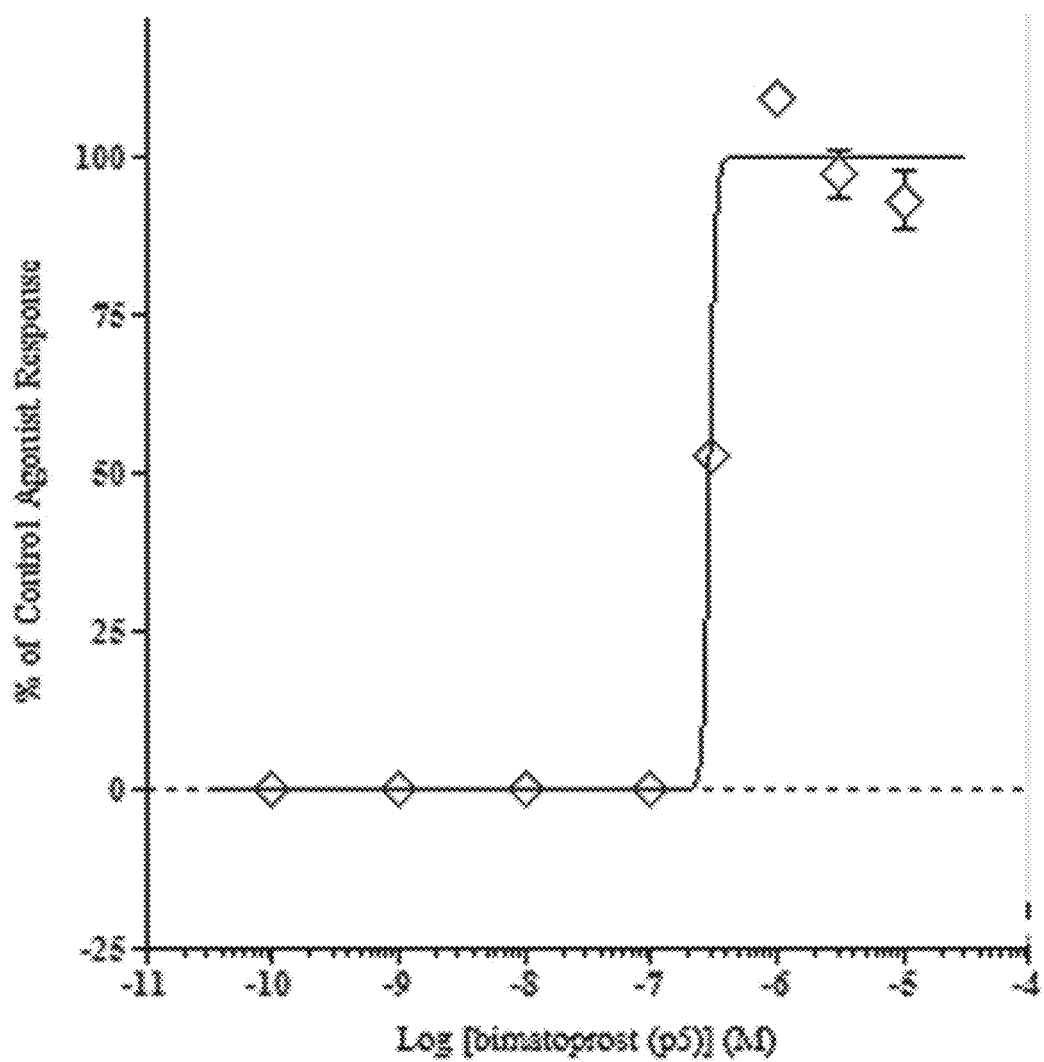
Figure 1C:
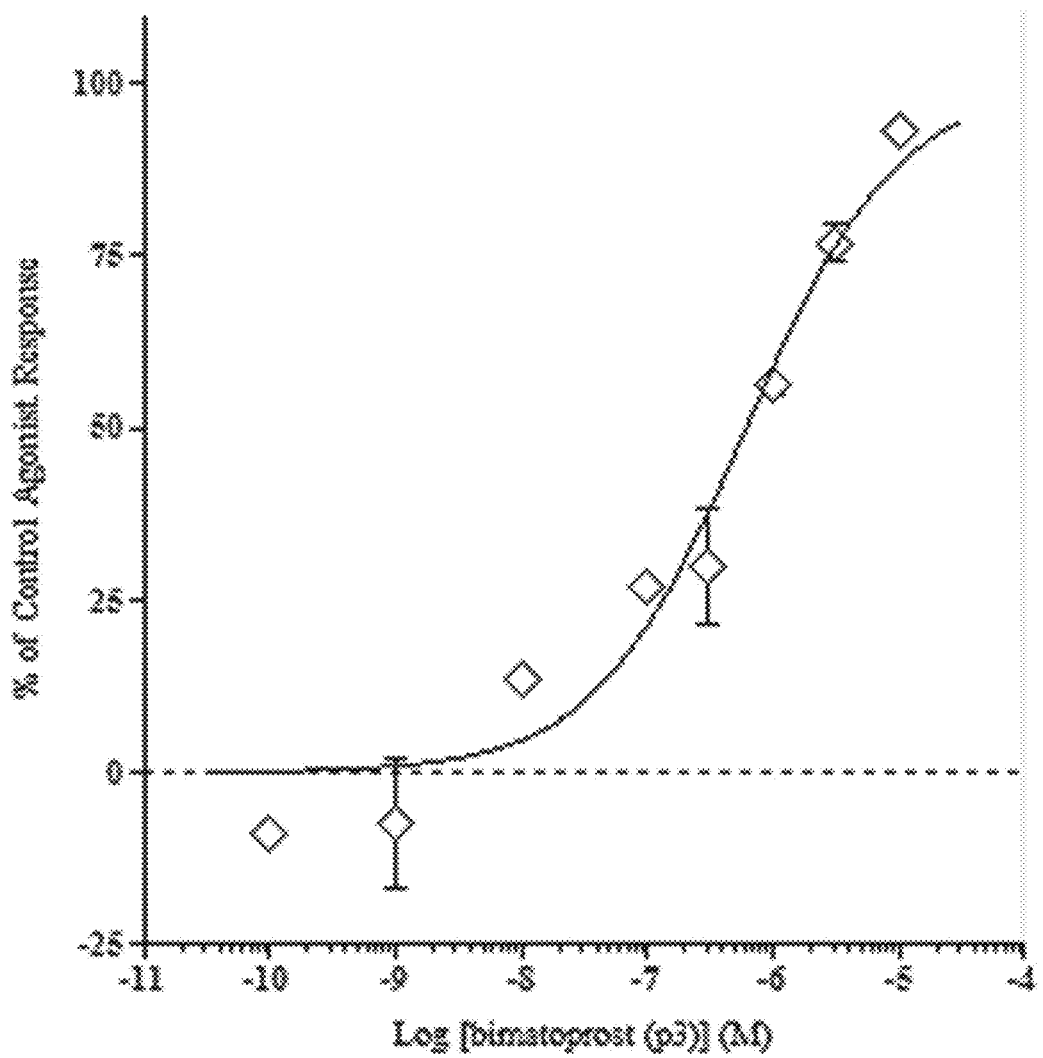
Figure 1D:
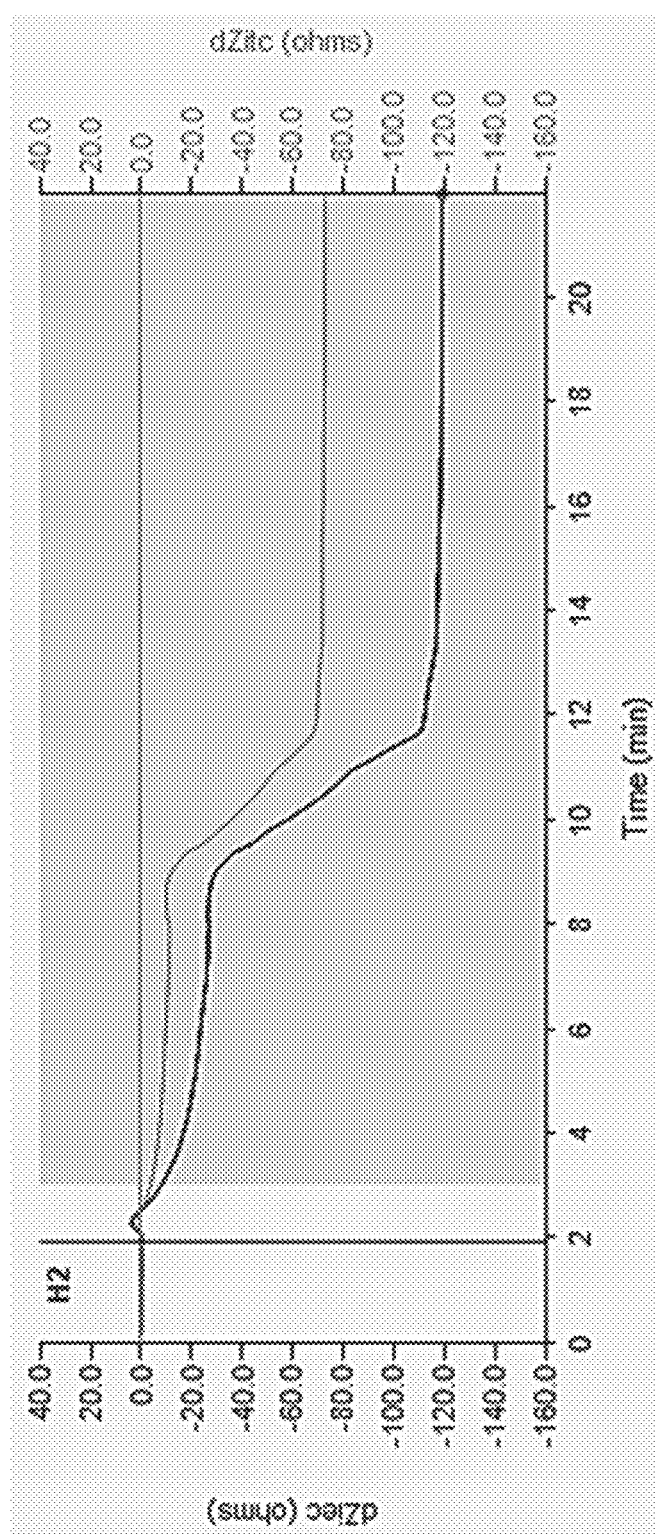
Figure 2A:
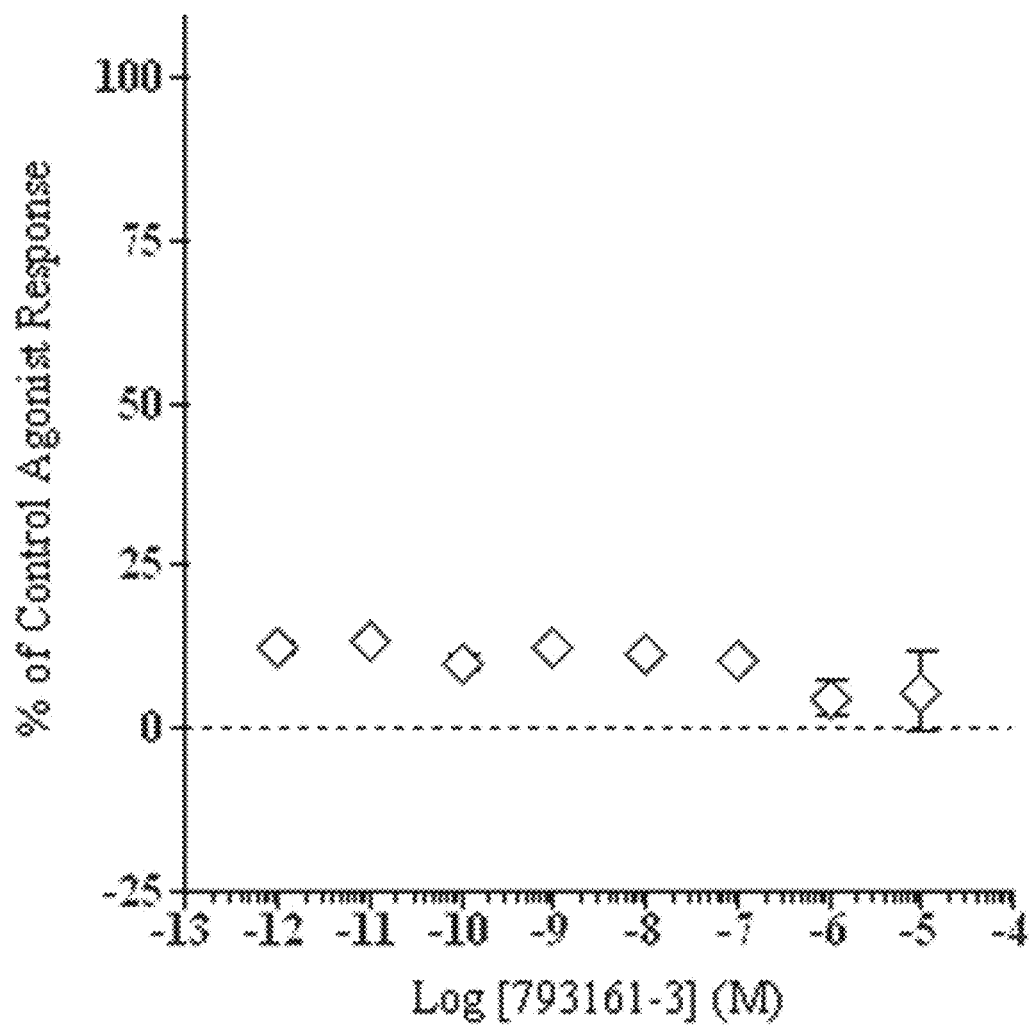
FIG. 2A, FIG. 2B, FIG. 2C, and FIG. 2D show the results of agonist response in the triplicate impedance assays (FIGS. 2A, 2B, and 2C) and signature trace of the top dose (FIG. 2D) with human dermal papilla cells in an in vitro cell dielectric spectroscopy assay with the compound of Formula II as described herein.
Figure 2B:
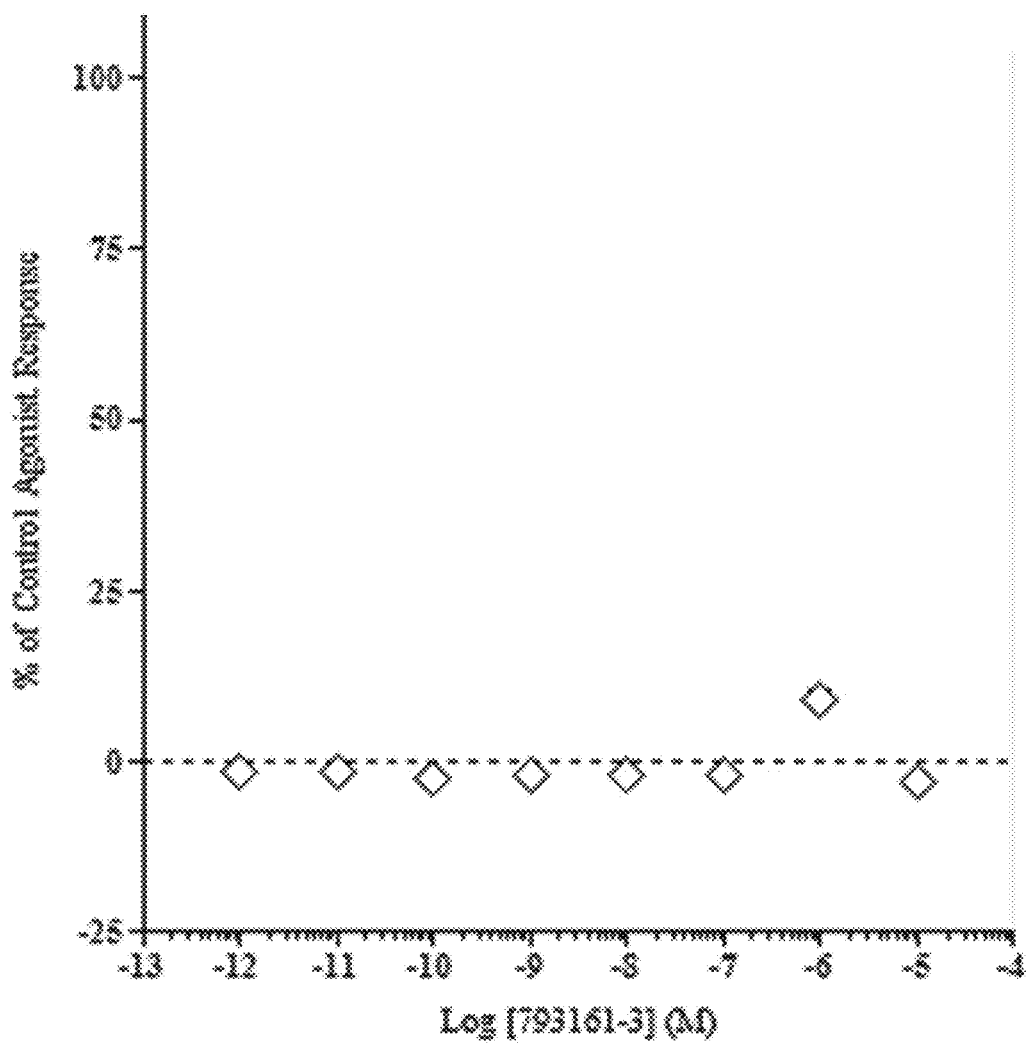
Figure 2C:
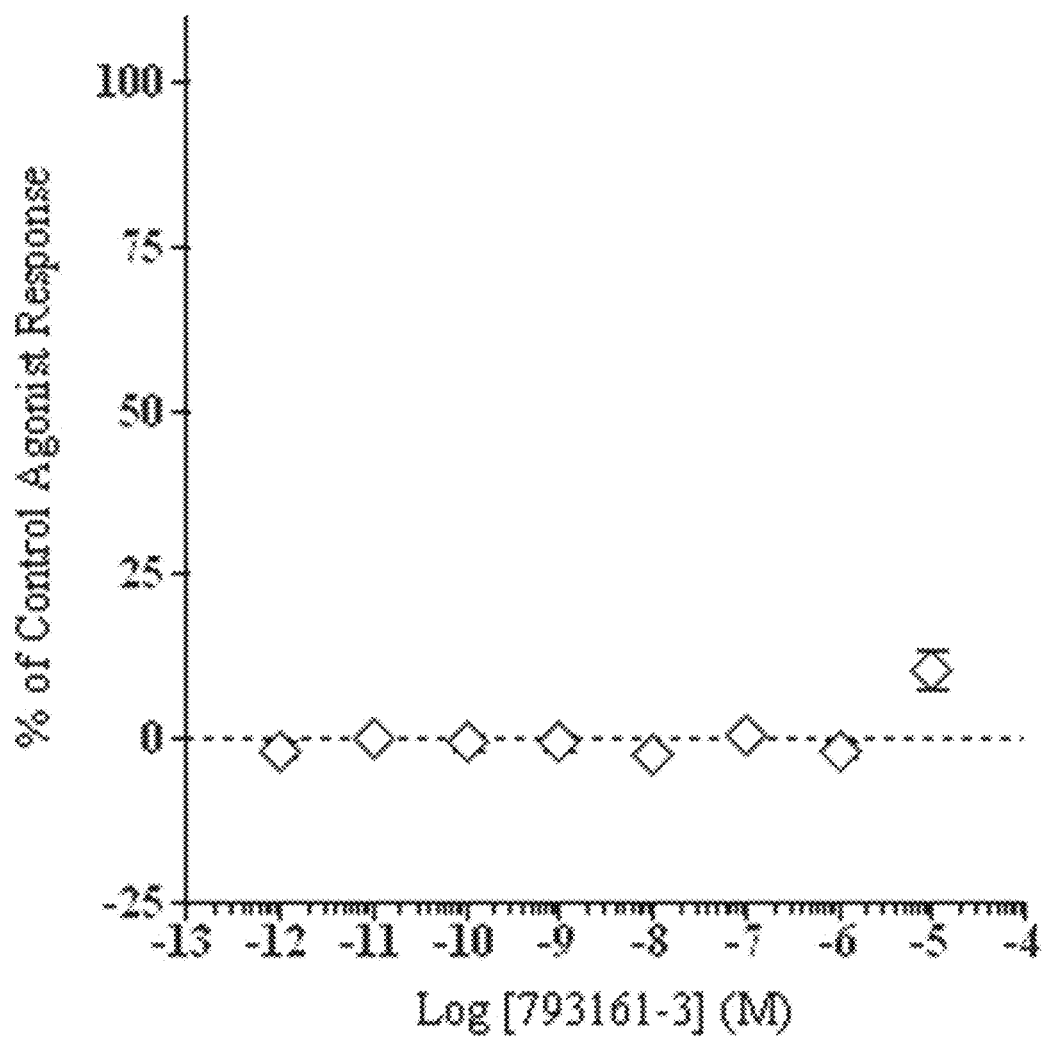
Figure 2D:
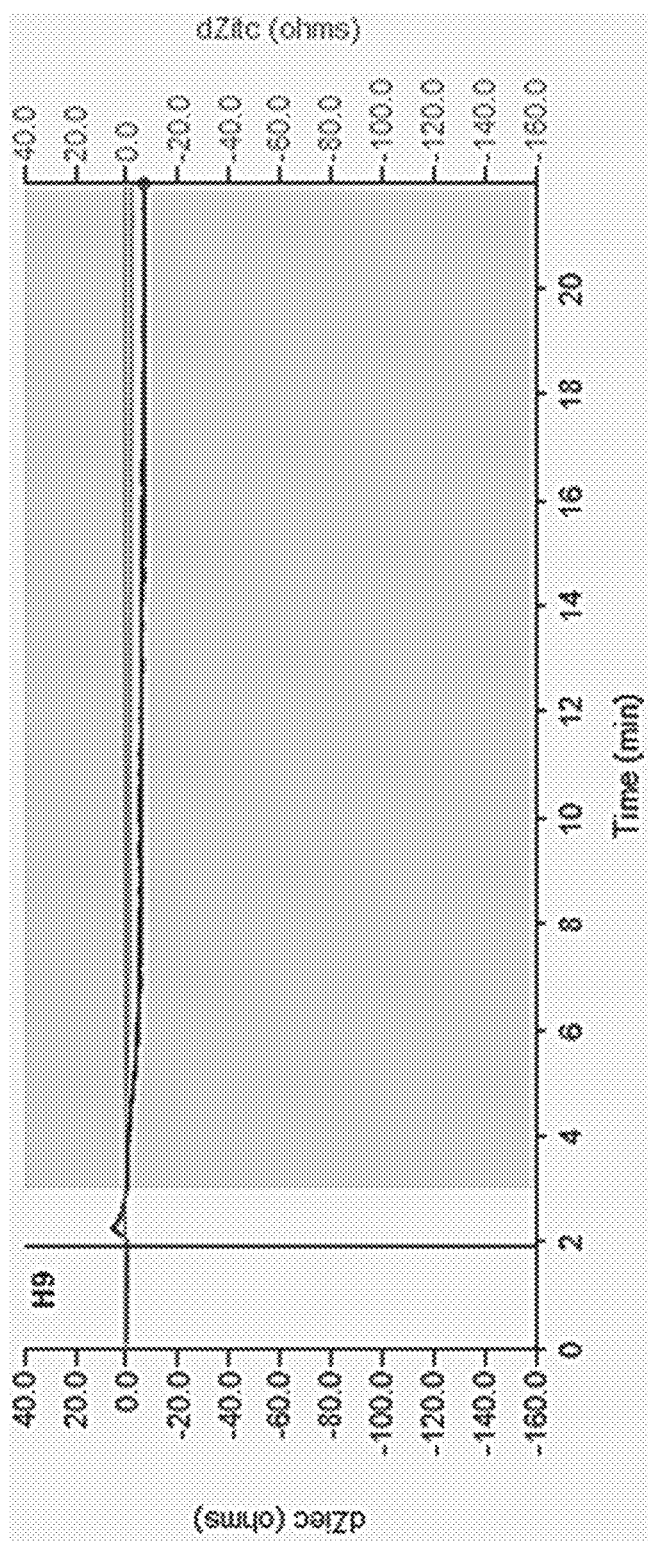
Figure 3A:
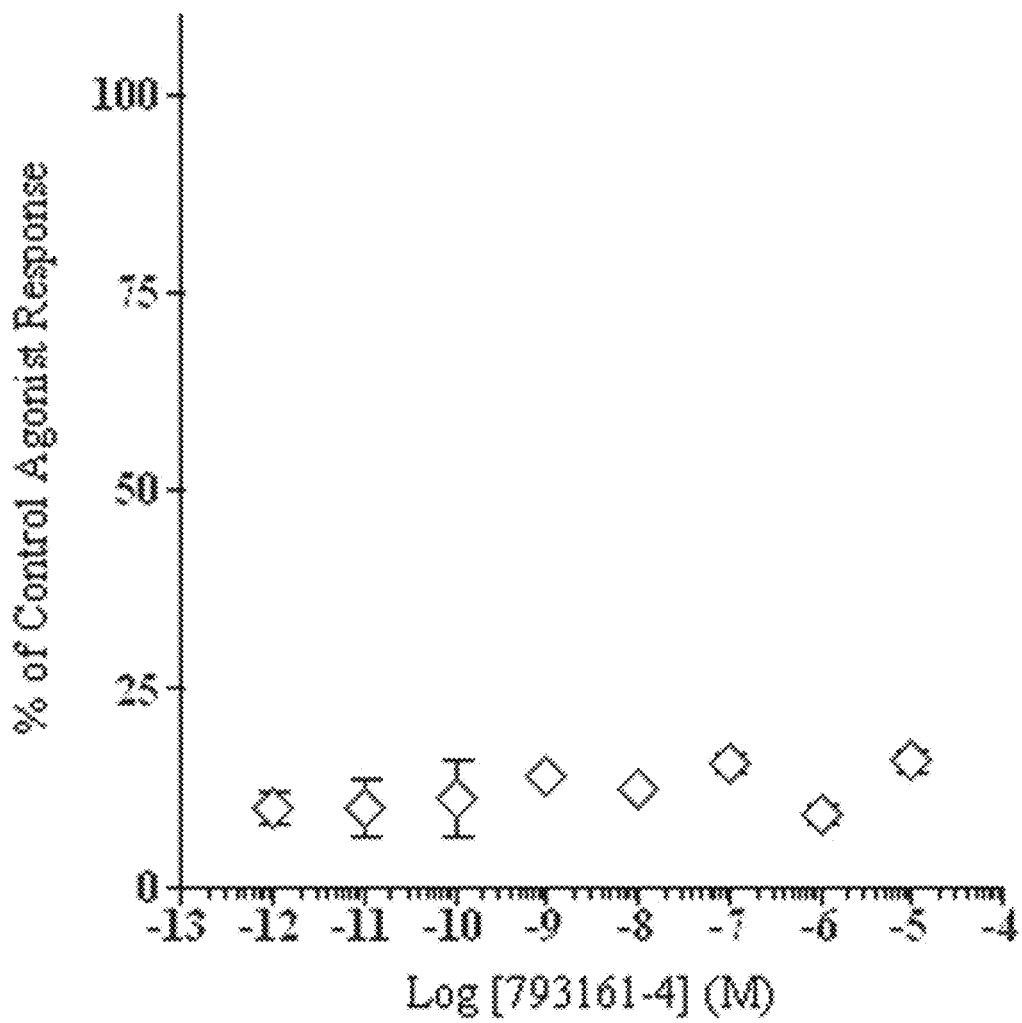
FIG. 3A, FIG. 3B, FIG. 3C, and FIG. 3D show the results of agonist response in the triplicate impedance assays (FIGS. 3A, 3B, and 3C) and signature trace of the top dose (FIG. 3D) with human dermal papilla cells in an in vitro cell dielectric spectroscopy assay with the compound of Formula II as described herein.
Figure 3B:
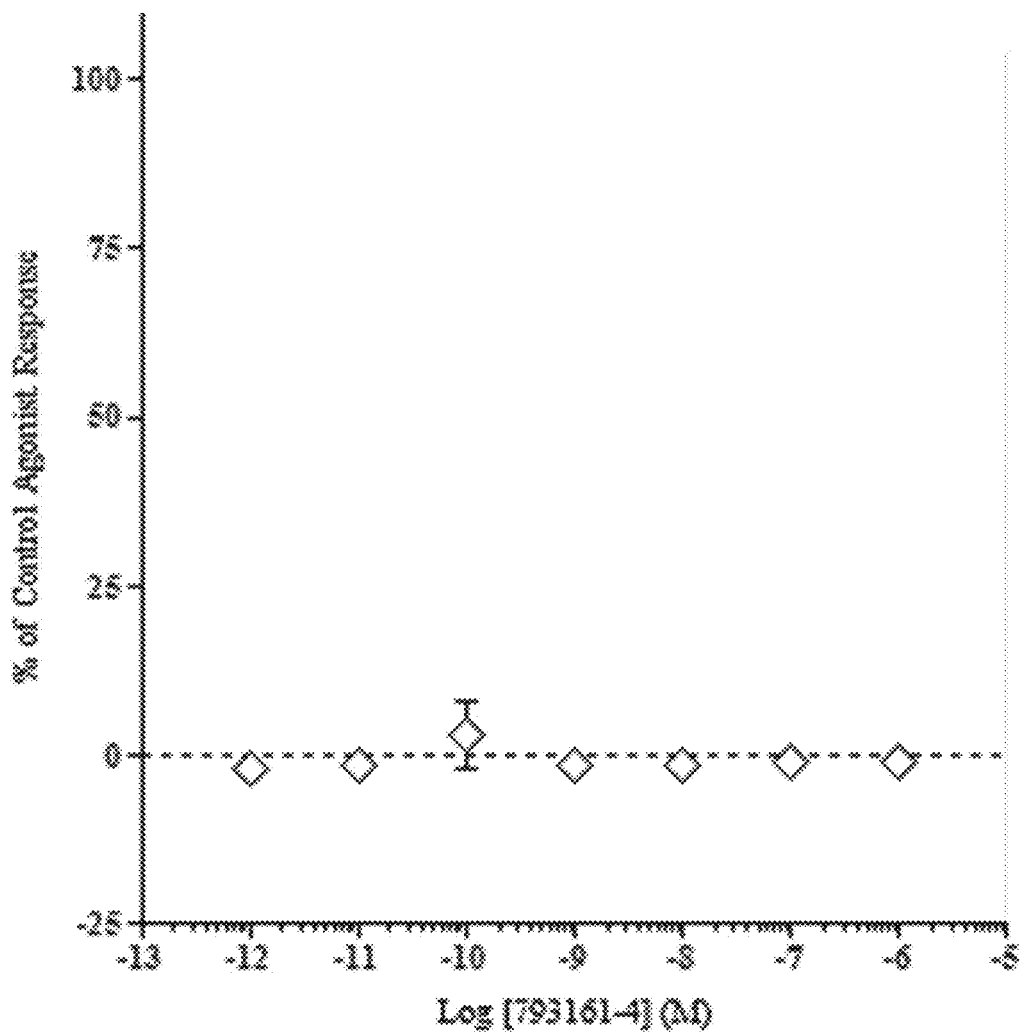
Figure 3C:
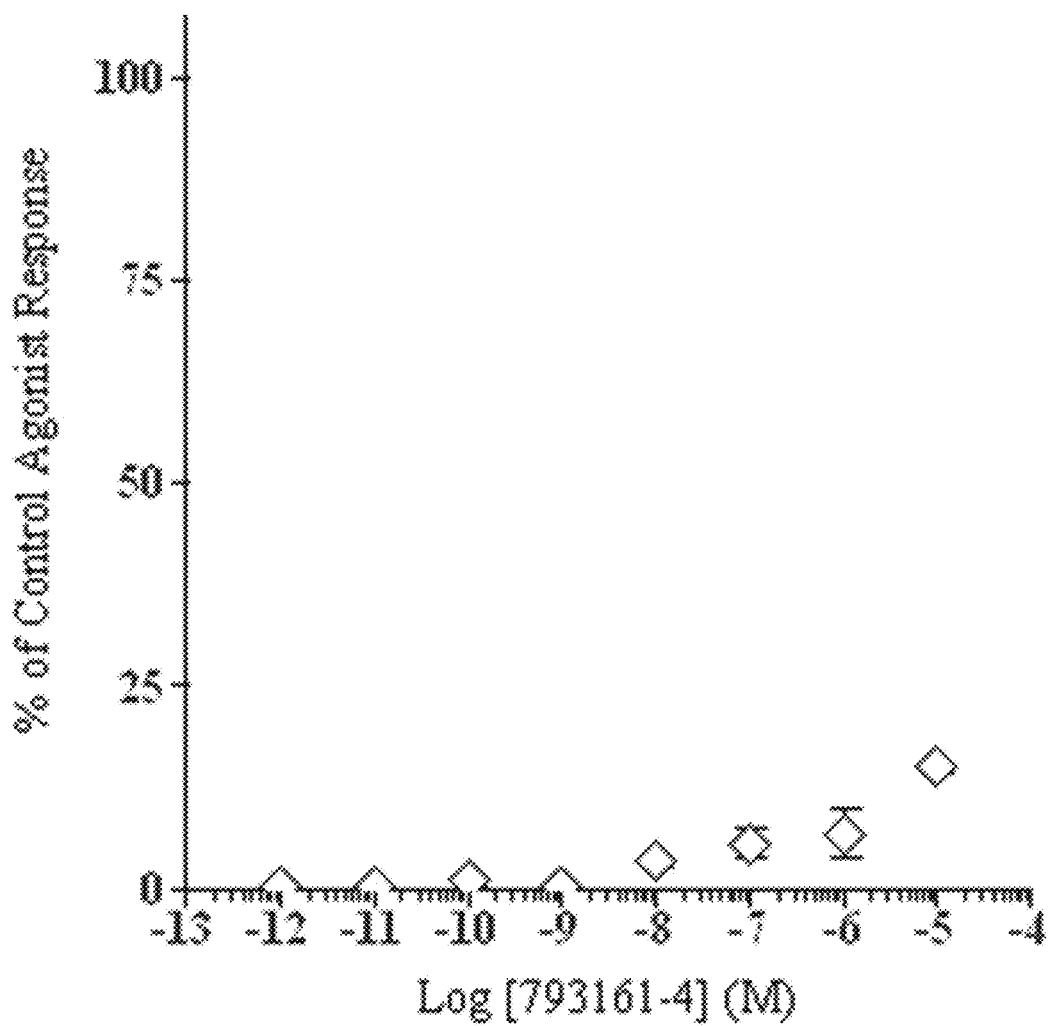
Figure 3D:
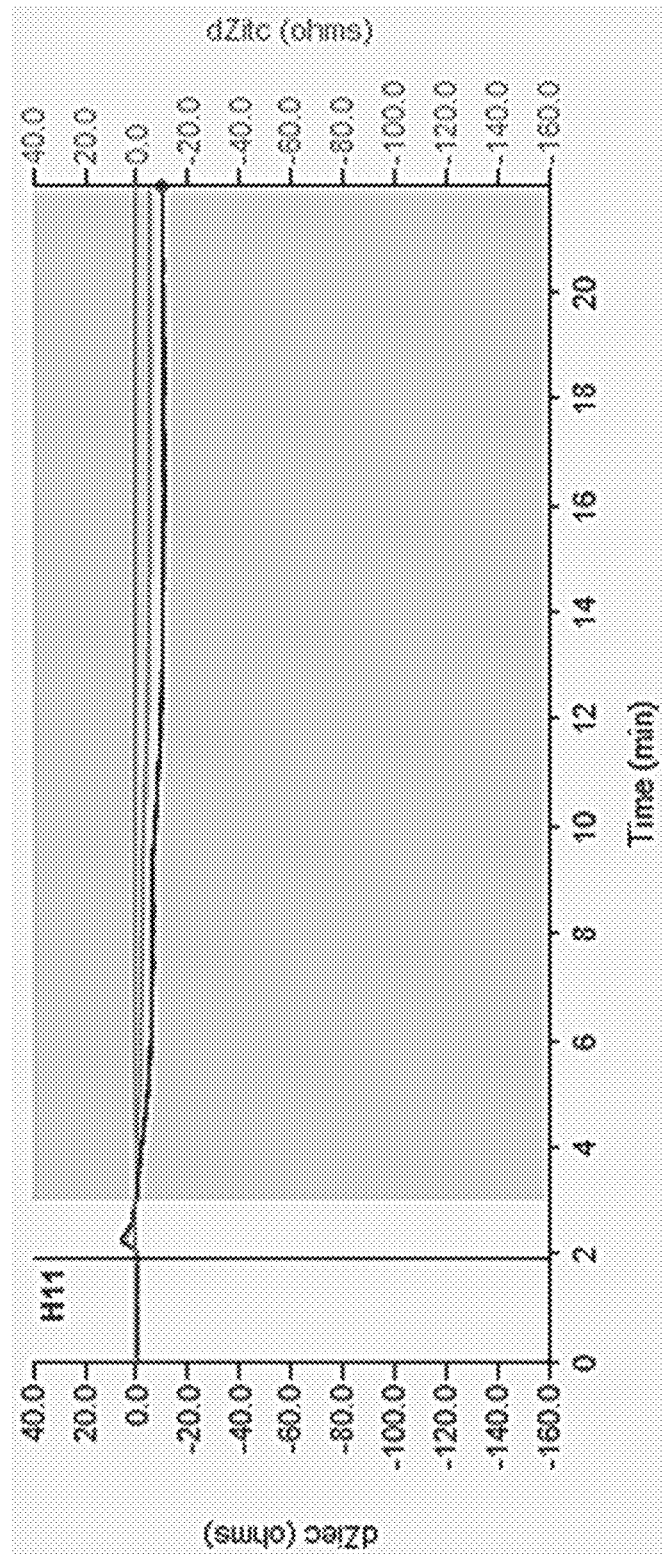

It is to be understood that both the foregoing general description and the following detailed description are exemplary and explanatory only and are not restrictive of the present disclosure. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques can be used for chemical syntheses, chemical analyses, and formulation.

In some embodiments, the methods described herein include a method of reducing body fat in a subject comprising administering to a subject in need of reducing body fat an effective amount compound of Formula I, a compound of Formula II, or a mixture thereof:

The term "body fat" as used herein refers the loose connective tissue known as "adipose tissue". Body fat can be present throughout the body of an individual, for example, beneath the skin (subcutaneous fat; e.g. cellulite), around internal organs (visceral fat), in bone marrow (yellow bone marrow), in breast tissue (breast fat), around the waist (waist fat; e.g. "love handles"), under the chin (submental fat), thigh tissue (thigh fat), and other regions of the body as would be identifiable to a skilled person (e.g. HIV associated lipodystrophy, steatoblepharon, and others).

The amount of body fat in an individual can be determined and/or estimated by a variety of methods identifiable to a skilled person. For example, body fat percentage (mass of body fat divided by body mass) can be estimated by techniques known to a skilled person such as hydrostatic (underwater) weighing, whole-body air displacement plethysmography, near-infrared interactance, dual energy X-ray absorptiometry, body average density measurement (in conjunction with use of the Brozek or Siri formulas), bioelectrical impedance analysis, anthropometric methods (e.g. skinfold measurements, ultrasound measurements, and estimations based on the subject's body mass index), magnetic resonance imaging, computed tomography, and other methods identifiable to a skilled person. Additionally, though not a direct measurement of body fat amount, an individual's body mass index (BMI) can also be indicative of the amount of body fat in an individual. Additionally, visual inspection can also reveal accumulated body fat such as in cellulite which can also be used as part of a quantitative measurement of cellulite (see, for example, Smalls et al. *J. Cosmet. Sci.* 2005, 56, 105-120). Additional methods for determining and/or estimating the amount of body fat will be identifiable to a skilled person.

The term "subject" as used herein refers to human or non-human animal. A subject is "in need of reducing body fat" if the individual desires, is advised, or otherwise requires a reduction in body fat either for therapeutic or for cosmetic reasons.

The term "reducing" as in "reducing body fat" as used herein refers to a lowering in the amount, mass, or volume of body fat. Such reduction can be measured and determined by measuring the amount of fat according to one or more of the methods described herein at an initial time point prior to the administering of the compounds described herein (e.g. compounds of Formulas I or II) and then measuring the amount of body fat at various time points (e.g. during the period of administering the compounds described herein as well after the administering has ceased). For example, a subject's body weight can be measured prior to beginning a treatment regimen with the compounds described herein and then measured during and after the treatment regimen. A decrease in body weight is indicative of a reduction in body fat. Similarly, skinfold measurements and/or other techniques (e.g. magnetic resonance imaging and/or computerized tomography) can be made or performed along with the weight measurements where a decrease in the parameters measured by those techniques (i.e. body fat percentage) is indicative of fat reduction. Additionally, the reduction of fat can be determined qualitatively such as by photographing the whole body, or portions of the body, at various time points before, during, and after a treatment regimen where the reduction in fat can be determined by visual inspection of the images (e.g. by seeing a visible reduction and in the size and/or volume of a particular fat deposit such as submental fat, waist fat, cellulite, and other forms of body fat amenable to visual inspection).

In some embodiments, the reduction of body fat achieved with the compounds of the present disclosure can occur without substantial hair growth or additional hair growth at the site of fat reduction. The term "hair growth" as used herein refers to an increase in the number of hairs in a given area of skin, an increase in the thickness of the hairs already present in a given area of skin, and increase in the length of hairs already present in a given area of skin, or combinations thereof. In particular, the number of hairs in a given area of skin can be counted by visual inspection, by the use of computerized methods such as TrichoScan (trichoscan.com/pages/english/home.php), by punch biopsy, and by other methods identifiable to a skilled person to determine the total number of hairs in a particular region, the total hair density (e.g. number of hairs per square centimeter), and other measurements of the number of hairs in a given area of skin identifiable to a skilled person (see, e.g., U. Blume-Peytavi et al. "Hair Growth Assetment Techniques" in *Hair Growth and Disorders*, U. Blume-Peytavi et al., Eds. Springer: New York 2008, Chapter 8). Similarly, the thickness of hairs already present in a given area of skin can also be measured by visual inspection, by the use of computerized methods such as TrichoScan, by punch biopsy, and by other methods identifiable to a skilled person to determine the thickness of the hairs (e.g. the thickness in μm of the hairs). Similarly, the length of the hairs already present in a given area of skin can also be measured by visual inspection, by the use of computerized methods such as TrichoScan, by punch biopsy or by other methods identifiable to a skilled person to determine the length of the hairs (e.g. the length in mm of the hairs and/or the linear hair growth rate in mm/day). Furthermore, hair thickness and hair length can also be characterized as a distribution wherein different fractions of hairs can show different thicknesses and/or lengths which can be plotted as a histogram which can be used to determine measurements such as average hair thickness and/or length and cumulative hair thickness and/or length (see, e.g. R. Hoffmann "TrichoScan: a novel tool for the analysis of hair growth in vivo" *J. Investig. Dermatol. Symp. Proc.* 2003, 109-115).

In addition, the amount of hair growth measured, whether measurement of the number, thickness, or length of hairs, or a combination thereof, can be used as part of methods of measurement of hair growth such as the Ferriman-Gallwey Index (Ferriman D M, Gallwey J D. Clinical assessment of body hair growth in women. *J Clin Endocrinol* 1961:21: 1440-1447; see also hirsutism.com/hirsutism-biology/ferriman-gallwey-score.shtm). In particular, the Ferriman-Gallwey Index can be used as a representation of hair growth in a male pattern on a woman shown in four different degrees of severity in 19 different body regions: namely the upper lip, chin, sideburns, neck, chest, upper back, lower back, buttocks, upper abdomen, lower abdomen, inguinal area, perianal area, arm, forearm, thigh, leg, foot, toes, and fingers wherein a value of 0 (zero) indicates an absence of terminal hair and wherein a value of 1-4 is assigned to each of the 19 regions depending on the amount of hair present (see N. F. Goodman et al. "American Association of Clinical Endocrinologists Medical Guidelines for Clinical Practice for The Diagnosis and Treatment of Hyperandrogenic Disorders" *Endocrine Practice* 2001, 7, 102-134).

The term "without substantial hair growth" as used herein in connection with the fat reduction achieved by administration of compounds described herein can, in some embodiments, refer to the substantial lack of hair growth in a region of skin at the site of fat reduction which did not previously have hair present. Additionally, the term "without additional hair growth" as used herein in connection with the fat reduction achieved by administration of compounds described herein can, in some embodiments, refer to the substantial lack of additional hair growth in a region of skin at the site of fat reduction where at least some hair is already present. In particular, the lack of additional hair growth is relative to any normal hair growth which would have occurred in absence of the administration of the compounds described herein. By way of example, if one or more of the compounds described herein are administered to a region which has a certain number of hairs per unit area (e.g. as determined by methods such as visual inspection and/or computerized methods such as TrichoScan, or by determination of a Ferriman-Gallwey Index value of 1 or more), then any fat reduction, measured by fat reduction determination methods described herein, can be considered to have occurred without additional hair growth if the site of administration shows a reduction in fat but substantially no new hairs present relative to the state of the region prior to administration of the compounds (e.g., there will be no hairs present as seen by methods such as visual inspection and/or computerized methods such as TrichoScan, and/or the Ferriman-Gallwey Index value would still be considered to be the previous value), or if the number of new hairs would not be substantially greater than the normal number of new hairs that would have been expected if the one or more compounds had not been administered. Thus, in some embodiments, even if additional new hairs are counted in addition to the number of hairs already present at the site prior to administration, if the site would have been expected to have a normal increase of about 1% to about 10% in the number of hairs (relative to the original number of hairs) if the one or more compounds had not been administered, then the fat reduction can be considered to occur without additional hair growth if the administration of the one or more compounds also resulted in hair growth that was not more than about 1% to about 10% (relative to the original number of hairs present prior to the one or more compounds being administered).

Similarly, by way of another example, fat reduction occurring due to the administration of one or more of the compounds described herein can be considered to occur without additional hair growth if the fat reduction occurs substantially without a change in the thickness of the hair (e.g. the average thickness, cumulative thickness, and/or distribution of hair thicknesses as determined by the visual and/or computerized methods described herein or as determined as part of the Ferriman-Gallwey Index) relative to the thickness of the hairs at the site of fat reduction prior to the administration of the one or more compounds. Additionally, the fat reduction can also be considered to occur without additional hair growth if change in thickness of the hair is not substantially greater than normal change in hair thickness that would have been expected if the one or more compounds had not been administered. Thus, in some embodiments, even if the thickness of the hairs at the site prior to administration increases, if the hairs at the site would have been expected to have a normal thickness increase of about 1% to about 10% (relative to the original thickness of hairs) if the one or more compounds had not been administered, then the fat reduction can be considered to occur without additional hair growth if the administration of the one or more compounds also resulted in hair thickness increase that was not more than about 1% to about 10% (relative to the original thickness of hairs prior to the one or more compounds being administered).

Similarly, by way of another example, fat reduction occurring due to the administration of one or more of the compounds described herein can be considered to occur without additional hair growth if the fat reduction occurs without a substantial change in the length of the hair relative to the length of the hairs (e.g. the average length, cumulative length, and/or distribution of hair lengths as determined by the visual and/or computerized methods described herein or as determined as part of the Ferriman-Gallwey Index) at the site of fat reduction prior to the administration of the one or more compounds. Additionally, the fat reduction can also be considered to occur without additional hair growth if change in length of the hair is not greater than normal change in hair length that would have been expected if the one or more compounds had not been administered. Thus, in some embodiments, even if the length of the hairs at the site prior to administration increases, if the hairs at the site would have been expected to have a normal length increase of about 1% to about 10% (relative to the original length of hairs) if the one or more compounds had not been administered, then the fat reduction can be considered to occur without additional hair growth if the administration of the one or more compounds also resulted in hair thickness increase that was not more than about 1% to about 10% (relative to the original thickness of hairs prior to the one or more compounds being administered).

A skilled person will also understand that hair growth can be a combination of increases in number of hairs, thickness of hairs, and lengths of hairs. Thus, fat reduction achieved by administration of the compounds described herein can occur without additional hair growth if there is no substantial increase in one or more parameters such as number of hairs, thickness of hairs, or length of hairs, and/or if the change in the one or more parameters is not more than would normally be expected, as described herein, if the one or more compounds had not been administered.

Furthermore, in some embodiments, the fat reduction occurring due to the administration of one or more compounds described herein can occur with less hair growth (e.g. number of hairs, thickness of hairs, and/or length of hairs) than occurs with the administration of other compounds which cause fat reduction but can also cause hair growth (e.g. bimatoprost). By way of example, administration of the compounds described herein can be considered to occur without additional hair growth if the fat reduction occurs with hair growth at the site of fat reduction that is between 0 and 15%, 0 and 10%, or 0 and 5% of the hair growth seen with the administration of the other compound that results in a comparable amount of fat reduction (e.g. results in an amount of fat reduction that is does not vary by more than about 0 to 20% relative to the amount of fat reduction achieved with the other compound).

The term "administering" as used herein refers to introduction of a substance (e.g. the compounds of Formulas I and II described herein) into a body of a subject and/or application of a substance onto the body of a subject by a particular route. Routes of administration would be identifiable to a skilled person and include, for example, oral administration, parenteral administration (e.g. subcutaneous injection, intramuscular injection, and intravenous injection), sublingual administration, buccal administration, rectal administration, ocular administration, optic administration, inhalation routes (e.g. inhaling a mist containing the substance though the mouth or nose), topical administration, transdermal administration (e.g. via transdermal patches), administration via an implant device, and others identifiable to a skilled person.

Administration can be "local" when the compound is administered to a particular localized region of the body and only that region near the site of administration is exposed to the compound (e.g. topical application or subcutaneous application to a particular region of the subject's body.)

Similarly, administration can be "systemic" when the compound is administered such that the compound is exposed throughout the subject's body and may be found in one or more regions distant from the site of administration (e.g. orally or intravenously administering the compound such that the compound will be distributed in the blood and throughout various tissues and/or body regions resulting in fat reduction at those tissues and/or regions).

In some embodiments, the compounds can be administered by administering pharmaceutical compositions to a subject. The pharmaceutical compositions can contain at least one compound described herein in a pharmaceutically acceptable carrier thereof and can in some embodiments contain one or more pharmaceutically acceptable excipients. The phrase "pharmaceutically acceptable" means the carrier, diluent or excipient is compatible with the other ingredients of the formulation and not deleterious to the recipient thereof.

Pharmaceutical compositions of the compounds described herein can be used in the form of a solid, a solution, an emulsion, a dispersion, a patch, a micelle, a liposome, and others identifiable to a skilled person, wherein the resulting composition contains one or more compounds described herein, as an active ingredient, in admixture with an organic or inorganic carrier or excipient suitable for enteral or parenteral applications. Compounds described herein can be combined, for example, with non-toxic, pharmaceutically acceptable carriers known to a skilled person for tablets, pellets, capsules, suppositories, solutions, emulsions, suspensions, and any other form suitable for use identifiable to a skilled person. Exemplary carriers which can be used can include glucose, lactose, gum acacia, gelatin, mannitol, starch paste, magnesium trisilicate, talc, corn starch, keratin, colloidal silica, potato starch, urea, medium chain length triglycerides, dextrans, and other carriers identifiable to a skilled person suitable for use in manufacturing preparations, in solid, semisolid, or liquid form. In addition, auxiliary agents, stabilizing agents, thickening agents, coloring agents, and perfumes can be used. Compounds described herein can be included in the pharmaceutical composition in an amount sufficient to produce the desired effect upon the subject's condition (e.g. fat reduction as described herein).

Pharmaceutical compositions containing compounds described herein can be in a form suitable for oral use, for example, as tablets, troches, lozenges, aqueous or oily suspensions, dispersible powders or granules, emulsions, hard or soft capsules, or syrups or elixirs, as well as others identifiable to a skilled person. Compositions intended for oral use can be prepared according to any method known in the art, and others identifiable to a skilled person, for the manufacture of pharmaceutical compositions and such compositions can contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing compounds described herein in admixture with non-toxic pharmaceutically acceptable excipients can also be manufactured by known methods. The excipients used can be, for example, (1) inert diluents such as calcium carbonate, lactose, calcium phosphate or sodium phosphate, or others identifiable to a skilled person; (2) granulating and disintegrating agents such as corn starch, potato starch or alginic acid, or others identifiable to a skilled person; (3) binding agents such as gum tragacanth, corn starch, gelatin or acacia, or others identifiable to a skilled person, and (4) lubricating agents such as magnesium stearate, stearic acid or talc, or others identifiable to a skilled person. The tablets can be uncoated or they can be coated by known techniques identifiable to a skilled person to delay disintegration and absorption in the gastrointestinal tract and thereby provide a sustained action over a longer period. For example, a time delay material such as glyceryl monostearate or glyceryl distearate can be employed.

In some cases, formulations for oral use can be in the form of hard gelatin capsules wherein the compounds described herein are mixed with an inert solid diluent, for example, calcium carbonate, calcium phosphate or kaolin, or others identifiable to a skilled person. Formulations can also be in the form of soft gelatin capsules wherein the compounds described herein are mixed with water or an oil medium, for example, peanut oil, liquid paraffin or olive oil, or others identifiable to a skilled person.

The pharmaceutical compositions can be in the form of a sterile injectable suspension. This suspension can be formulated according to known methods identifiable to a skilled person using suitable dispersing or wetting agents and suspending agents. The sterile injectable preparation can also be a sterile injectable solution or suspension in a non-toxic parenterally acceptable diluent or solvent, for example, as a solution in 1,3-butanediol, or other non-toxic parenterally acceptable diluents or solvents identifiable to a skilled person. Sterile, fixed oils are conventionally employed as a solvent or suspending medium. For this purpose, a bland fixed oil can be employed including synthetic mono- or diglycerides, fatty acids (including oleic acid), naturally occurring vegetable oils like sesame oil, coconut oil, peanut oil, cottonseed oil, and others identifiable to a skilled person, or synthetic fatty vehicles like ethyl oleate and others identifiable to a skilled person. Buffers, preservatives, antioxidants, and others identifiable to a skilled person can be incorporated as required.

Pharmaceutical compositions containing compounds described herein can be in a form suitable for topical use, for example, as oily suspensions, as solutions or suspensions in aqueous liquids or non-aqueous liquids, or as oil-in-water or water-in-oil liquid emulsions. Pharmaceutical compositions can be prepared by combining a therapeutically effective amount of at least one compound described herein as an active ingredient with conventional topically acceptable pharmaceutical excipients and by preparation of unit dosage suitable for topical use. Additional compositions that may be suitable for use herewith are described in U.S. Patent Application Publication No. 2014/0155488, titled "Compositions and methods for stimulating hair growth", the disclosure of which is hereby incorporated by reference.

The compounds described can also be administered in the form of suppositories for rectal administration of the compounds. These compositions can be prepared by mixing the compounds described herein with a suitable non-irritating excipient, such as, for example, cocoa butter, synthetic glyceride esters of polyethylene glycols, which are solid at ordinary temperatures, but liquefy and/or dissolve in the rectal cavity to release the compounds.

Since individual subjects can present a wide variation amount of fat to be reduced and each compound has its unique characteristics, the precise mode of administration and dosage employed for each subject is left to the discretion of the practitioner.

In some embodiments, when the compounds described herein (e.g. compounds of Formula I and Formula II) are part of a composition, the compounds are the only active ingredients which result in fat reduction, and in particular fat reduction without significant hair growth and/or additional hair growth as described herein. The term "active ingredient" as used herein refers to a component which is responsible for the biological effect of fat reduction, and in particular fat reduction without significant hair growth and/or additional hair growth as described herein, whereas the other components of the composition (e.g. excipients, carriers, and diluents) are not responsible for the biological effect of fat reduction, and in particular fat reduction without significant hair growth and/or additional hair growth as described herein, even if they have other functions in the composition which are necessary or desired as part of the formulation (such as lubrication, flavoring, pH control, emulsification, and other functions other than fat reduction and in particular fat reduction without significant hair growth and/or additional hair growth as described herein).

The term "effective amount" as used herein refers to an amount of a compound (e.g. the compounds of Formula's I and II) which will exert a beneficial effect when administered to an individual. For example, a given amount of a compound will be an "effective amount" when administration of that amount of the compound results in the reduction of fat in a subject as determined by the measurement and evaluation techniques described herein. In particular, in some embodiments, the effective amount not only results in reduction of fat, but also does so without significant hair growth and/or additional hair growth as described herein and which can be seen with certain compounds such as bimatoprost.

The effective amount can be administered as described herein. For example, the effective amount can be formulated as a pharmaceutical composition and injected subcutaneously into a particular deposit of fat on the body to reduce the fat in the particular region. Alternatively, the effective amount can be formulated as part of a composition for topical administration (e.g. a cream or gel) and be topically administered to a particular fat deposit on the subject's body to reduce fat in that region. Alternatively, effective amount can be formulated as part of an oral formulation (e.g. a capsule) or parenteral formulation (e.g. an injectable formulation) and administered to a subject to achieve fat reduction in various regions of a subject's body.

In some embodiments, an effective amount of only a compound of Formula I can be administered. In other embodiments, an effective amount of only a compound of Formula II can be administered. In other embodiments, a combination of effective amounts of compounds according to Formulas I and II can be administered.

The actual amount of the compound to be administered in any given case will be determined by a physician or other skilled person taking into account the relevant circumstances, such as the amount of fat reduction, the age and weight of the patient, the patient's general physical condition, the cause of the condition, and the route of administration.

The actual effective amount of the active compounds described herein also depends on the specific compound, and on the amount of fat reduction desired. The selection of the appropriate dose is well within the knowledge of the skilled artisan upon a reading of the present disclosure and based on the general knowledge of the skilled artisan. For example, in some subjects a reduction in body fat percentage to be in a range of about 25-31% from a higher percentage in females, and to be a range of about 15-24% from a higher percentage in males, can be a desired goal. Further lowering can be desirable and can be discussed between the subject and their healthcare provider so as to reduce fat in a medically safe manner. The dosage amounts and treatment duration can then be selected based on the subject's goal and the healthcare provider's recommendation based on the medical knowledge of the healthcare provider. As another example, the amount of fat reduction can be an amount that results in at least about a 5% drop in body weight. As a further example, the amount of fat reduction can be an amount to result in a visible change in fat deposits (for example a visual reduction of submental fat, cellulite, abdominal fat, or waist fat). The compound can be administered in an effective amount until a desired visible change is achieved.

Unless indicated otherwise herein, the term "about" is intended to include values (e.g., weight percentages) proximate to the recited range that are equivalent (e.g. bioequivalent) in terms of the functionality of the individual ingredient (e.g. active ingredient or excipient), the composition, or the embodiment. Furthermore, as will be understood by a skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

Other therapeutically efficient amounts will be apparent to a skilled person upon a reading of the present disclosure. For example, a skilled person can determine the maximum safe dosage for healthy subjects based on the dosages used in animal studies by routine methods (see, e.g. Dept. of Health and Human Services "Guidance For Industry: Estimating the Maximum Safe Starting Dose in Initial Clinical Trials for Therapeutics in Adult Healthy Volunteers"), and then administer to subjects in need thereof various dosages below the maximum safe dosage by routine methods and experimentation until a dosage which results in a desirable effect (e.g. fat reduction without significant or additional hair growth) is reached. Exemplary effective amounts can be about 0.05 mg/kg to about 5 mg/kg. Additional effective amounts can be about 0.05 mg/kg to 1 mg/kg, 0.05 mg/kg to about 2 mg/kg, about 0.05 mg/kg to about 3 mg/kg, and about 0.05 mg/kg to about 4 mg/kg.

Still additional therapeutically effective amounts can be about 0.05 mg/kg to about 0.15 mg/kg, about 0.15 mg/kg to about 0.27 mg/kg, about 0.27 mg/kg to about 0.39 mg/kg, about 0.39 mg/kg to about 0.51 mg/kg, about 0.51 mg/kg to about 0.63 mg/kg, about 0.63 mg/kg to about 0.75 mg/kg, about 0.75 mg/kg to about 0.87 mg/kg, about 0.87 mg/kg to about 0.99 mg/kg, about 0.99 mg/kg to about 1.11 mg/kg, about 1.11 mg/kg to about 1.23 mg/kg, about 1.23 mg/kg to about 1.35 mg/kg, about 1.35 mg/kg to about 1.47 mg/kg, about 1.47 mg/kg to about 1.59 mg/kg, about 1.59 mg/kg to about 1.71 mg/kg, about 1.71 mg/kg to about 1.83 mg/kg, about 1.83 mg/kg to about 1.95 mg/kg, about 1.95 mg/kg to about 2.07 mg/kg, about 2.07 mg/kg to about 2.19 mg/kg, about 2.19 mg/kg to about 2.31 mg/kg, about 2.31 mg/kg to about 2.43 mg/kg, about 2.43 mg/kg to about 2.55 mg/kg, about 2.55 mg/kg to about 2.67 mg/kg, about 2.67 mg/kg to about 2.79 mg/kg, about 2.79 mg/kg to about 2.91 mg/kg, about 2.91 mg/kg to about 3.03 mg/kg, about 3.03 mg/kg to about 3.15 mg/kg, about 3.15 mg/kg to about 3.27 mg/kg, about 3.27 mg/kg to about 3.39 mg/kg, about 3.39 mg/kg to about 3.51 mg/kg, about 3.51 mg/kg to about 3.63 mg/kg, about 3.63 mg/kg to about 3.75 mg/kg, about 3.75 mg/kg to about 3.87 mg/kg, about 3.87 mg/kg to about 3.99 mg/kg, about 3.99 mg/kg to about 4.11 mg/kg, about 4.11 mg/kg to about 4.23 mg/kg, about 4.23 mg/kg to about 4.35 mg/kg, about 4.35 mg/kg to about 4.47 mg/kg, about 4.47 mg/kg to about 4.59 mg/kg, about 4.59 mg/kg to about 4.71 mg/kg, about 4.71 mg/kg to about 4.83 mg/kg, about 4.83 mg/kg to about 4.95 mg/kg, and about 4.95 mg/kg to about 5 mg/kg.

The therapeutically efficient amount can be present in a formulation (e.g. for topical administration) at between about 0.01 and about 5% (w/v). In some embodiments, the therapeutically effective amount in the formulation can be from about 0.01 to about 1%, about 0.01 to about 2%, about 0.01 to about 3%, and about 0.01 to about 4%. In other embodiments, the therapeutically effective amount in the formulation can be from about 0.01 to about 1%, about 1 to about 2%, about 2 to about 3%, about 3 to about 4%, about 4 to about 5%.

In other embodiments, the therapeutically effective amount in the formulation can be from about 0.01 to about 0.06%, about 0.06 to about 0.11%, about 0.11 to about 0.16%, about 0.16 to about 0.21%, about 0.21 to about 0.26%, about 0.26 to about 0.31%, about 0.31 to about 0.36%, about 0.36 to about 0.41%, about 0.41 to about 0.46%, about 0.46 to about 0.51%, about 0.51 to about 0.56%, about 0.56 to about 0.61%, about 0.61 to about 0.66%, about 0.66 to about 0.71%, about 0.71 to about 0.76%, about 0.76 to about 0.81%, about 0.81 to about 0.86%, about 0.86 to about 0.91%, about 0.91 to about 0.96%, about 0.96 to about 1.01%, about 1.01 to about 1.06%, about 1.06 to about 1.11%, about 1.11 to about 1.16%, about 1.16 to about 1.21%, about 1.21 to about 1.26%, about 1.26 to about 1.31%, about 1.31 to about 1.36%, about 1.36 to about 1.41%, about 1.41 to about 1.46%, about 1.46 to about 1.51%, about 1.51 to about 1.56%, about 1.56 to about 1.61%, about 1.61 to about 1.66%, about 1.66 to about 1.71%, about 1.71 to about 1.76%, about 1.76 to about 1.81%, about 1.81 to about 1.86%, about 1.86 to about 1.91%, about 1.91 to about 1.96%, about 1.96 to about 2.01%, about 2.01 to about 2.06%, about 2.06 to about 2.11%, about 2.11 to about 2.16%, about 2.16 to about 2.21%, about 2.21 to about 2.26%, about 2.26 to about 2.31%, about 2.31 to about 2.36%, about 2.36 to about 2.41%, about 2.41 to about 2.46%, about 2.46 to about 2.51%, about 2.51 to about 2.56%, about 2.56 to about 2.61%, about 2.61 to about 2.66%, about 2.66 to about 2.71%, about 2.71 to about 2.76%, about 2.76 to about 2.81%, about 2.81 to about 2.86%, about 2.86 to about 2.91%, about 2.91 to about 2.96%, about 2.96 to about 3.01%, about 3.01 to about 3.06%, about 3.06 to about 3.11%, about 3.11 to about 3.16%, about 3.16 to about 3.21%, about 3.21 to about 3.26%, about 3.26 to about 3.31%, about 3.31 to about 3.36%, about 3.36 to about 3.41%, about 3.41 to about 3.46%, about 3.46 to about 3.51%, about 3.51 to about 3.56%, about 3.56 to about 3.61%, about 3.61 to about 3.66%, about 3.66 to about 3.71%, about 3.71 to about 3.76%, about 3.76 to about 3.81%, about 3.81 to about 3.86%, about 3.86 to about 3.91%, about 3.91 to about 3.96%, about 3.96 to about 4.01%, about 4.01 to about 4.06%, about 4.06 to about 4.11%, about 4.11 to about 4.16%, about 4.16 to about 4.21%, about 4.21 to about 4.26%, about 4.26 to about 4.31%, about 4.31 to about 4.36%, about 4.36 to about 4.41%, about 4.41 to about 4.46%, about 4.46 to about 4.51%, about 4.51 to about 4.56%, about 4.56 to about 4.61%, about 4.61 to about 4.66%, about 4.66 to about 4.71%, about 4.71 to about 4.76%, about 4.76 to about 4.81%, about 4.81 to about 4.86%, about 4.86 to about 4.91%, about 4.91 to about 4.96%, and about 4.96 to about 5% (w/v).

The therapeutically effective amount can be administered according to a dosing frequency that is identifiable to a skilled person during a time period that is also identifiable to a skilled person. The term "dosing frequency" as used herein, refers to the number of times the compounds described herein are administered to a subject. Exemplary dosing frequencies include administering the effective amount at discrete times during a day such as, for example, once a day (QD), twice a day (BID), three times a day (TID), four times a day (QID), and others identifiable to a skilled person. Other exemplary dosing frequencies include continuous dosing, for example by intravenous infusion, use of a drug pump, use of a transdermal patch, or other methods of continuous dosing identifiable to a skilled person.

The therapeutically effective amount can be administered at a desired dosing frequency for a time period identifiable to a skilled person. For example, a therapeutically effective can be administered once or twice a day (or at another dosing frequency identifiable to a skilled person) for a set period of time (e.g. seven to fourteen days, two to four weeks, one to six months, or for another time period identifiable to a skilled person). As another example, a therapeutically effective amount can be administered once or twice a day (or at another dosing frequency identifiable to a skilled person) for a non-predetermined period of time. A skilled person can determine at various points during the period of time if the administration of the effective amount is to be continued (e.g., if a desired outcome such as a particular amount of fat loss has been achieved and administration of the effective amount is not required and/or desired anymore).

Some compounds described herein have at least one asymmetric center in their structure. This asymmetric center can be present in an R or S configuration, said R and S notation is used in correspondence with the rules described in *Pure Applied Chem.* 1976, 45, 11-13.

Reference to a compound or compounds described herein is intended to encompass that compound in each of its possible isomeric forms and mixtures thereof unless the particular isomeric form is referred to specifically.

Synthesis of compounds described herein (e.g. Formulas I and II) can be achieved by known methods, for example, those recited in WO1996/036599 and WO1997/031895.

In some embodiments, the compounds described herein can be used in the manufacture of a medicament for fat reduction in a subject.

Another embodiment is a kit comprising a composition comprising a compound disclosed herein, a container, and instructions for administration of said composition to a subject for fat reduction.

EXAMPLES

The following examples are intended only to illustrate the present disclosure and should in no way be construed as limiting the present disclosure.

Example 1: Lack of Activity on Human Dermal Papilla Cells

In this example, the lack of activity of the compound according to Formulas I and II is shown. In general, bimatoprost or the compound of Formula I was incubated at concentrations from $10^{-5}$ and $10^{-12}$ M with human dermal papilla cells in an in vitro impedance assay. Bimatoprost caused a down-ward signal (relaxation) or reduction in impedance, while the compound of Formula I did not produce any detectable effect. Three independent experiments were performed.

More specifically, Human Hair Dermal Papilla Cells (HHDPCs) were expanded in specific culture medium (Promo Cell). After growing, the cells were seeded on 96 well plates coated with poly-L-Lysine at 20,000 cells per well. Cells were incubated during 24 hours at 37° C., 5% $CO_2$. The day of the experiment, the culture medium was eliminated and replaced by HBSS containing BSA, 0.1% v/v. The cells were incubated in the CellKey system, for 4 hours at 28° C. before using to test compounds. Bimatoprost, the compound of Formula I, and/or the compound of Formula II were tested at 7 concentrations from $10^{-5}$ to $10^{-12}$ M. The change in impedance was measured over 20 minutes. The background was subtracted and the impedance signal was normalized to the reference (bimatoprost) for the compound of Formula I and the compound of Formula II. The data presented is in triplicate and of three independent experiments.

The results of the assay can be seen in FIGS. 1A-1D. Bimatoprost shows activity on primary human dermal papilla cells whereas compounds of Formulas I and II do not show activity (see FIGS. 2A-2D for the compound of Formula II and FIGS. 3A-3D for the compound of Formula I). These results indicate that the compounds according to Formulas I and II do not exhibit activity and thus do not activate receptors present on these cells. These cells are the primary driver of hair growth, for which stimulation by bimatoprost and other compounds, such as minoxidil, mediate their action (see, e.g., Khidhir et al. FASB J. 2013, 27, 557-567; Messenger et al. Br. J. Dermatol. 2004, 150, 186-194; and Li et al. J. Invest. Dermatol. 2001, 117, 1594-1600) the hair-growth associated with molecules such as bimatoprost.

Example 2: Lack of Acceleration of Time to Full Hair Growth

In this Example, it is shown that the compound of Formula I does not accelerate the time to full hair growth. In general, the compound of formula I and bimatoprost were prepared in the minoxidil formulation (50% Propylene Glycol; 30% Ethyl Alcohol) at a concentration of 0.03% for both compounds. Both compounds were given topically to shaved backs of mice (as described in Khidhir et al. FASEB J. 2013 27(2):557-567).

More specifically, female C57BL/6J mice (cat. no. 000664; Jackson Laboratory, Bar Harbor, Me., USA), aged 7 weeks, were randomly distributed into 4 groups to avoid any sibling bias and housed in groups of 5 with standard diet food pellets and water available ad libitum. Initially, dorsal hairs were removed externally by shaving (~2×6 cm) using an electric trimmer (Wahl Stylique Designer/Liner pet trimmer; 919179; Petco, San Diego, Calif., USA) revealing pink skin. From the next day, termed d 0 (zero), each mouse was treated topically with either the vehicle alone (ethanol: propylene glycol:water 3:5:2) or 0.03, 0.10, or 0.30% bimatoprost in the vehicle for d 14; 10 mice were used for each condition. The appropriate solution (70 µl) was rubbed gently into the dorsal skin of each mouse daily; new gloves were worn for each treatment type. Hair growth was recorded daily for each animal for d 42, and dorsal photographs were taken at d 0, 7, 14, 17, 21, 24, 28, 31, 35, and 42. The first day of anagen, defined as the first day when visible darkness could be seen that subsequently increased and progressed to visible black hair, was recorded for each animal. To calculate mean values, the first day of growth was designated as d 43 for any mouse showing no hair growth signs by the last day. The day when the shaved dorsal area was fully covered with new black hairs, i.e., there was no pink skin remaining and no visible difference in hair length to the adjacent unshaved areas, was also recorded. This assay has been successfully used to evaluate compounds that cause hair growth (see, e.g., Khidhir et al. FASB J. 2013, 27, 557-567; Plikus et al. J. Invest. Dermatol. 2008, 128, 1071-1080).

Figure 4A:
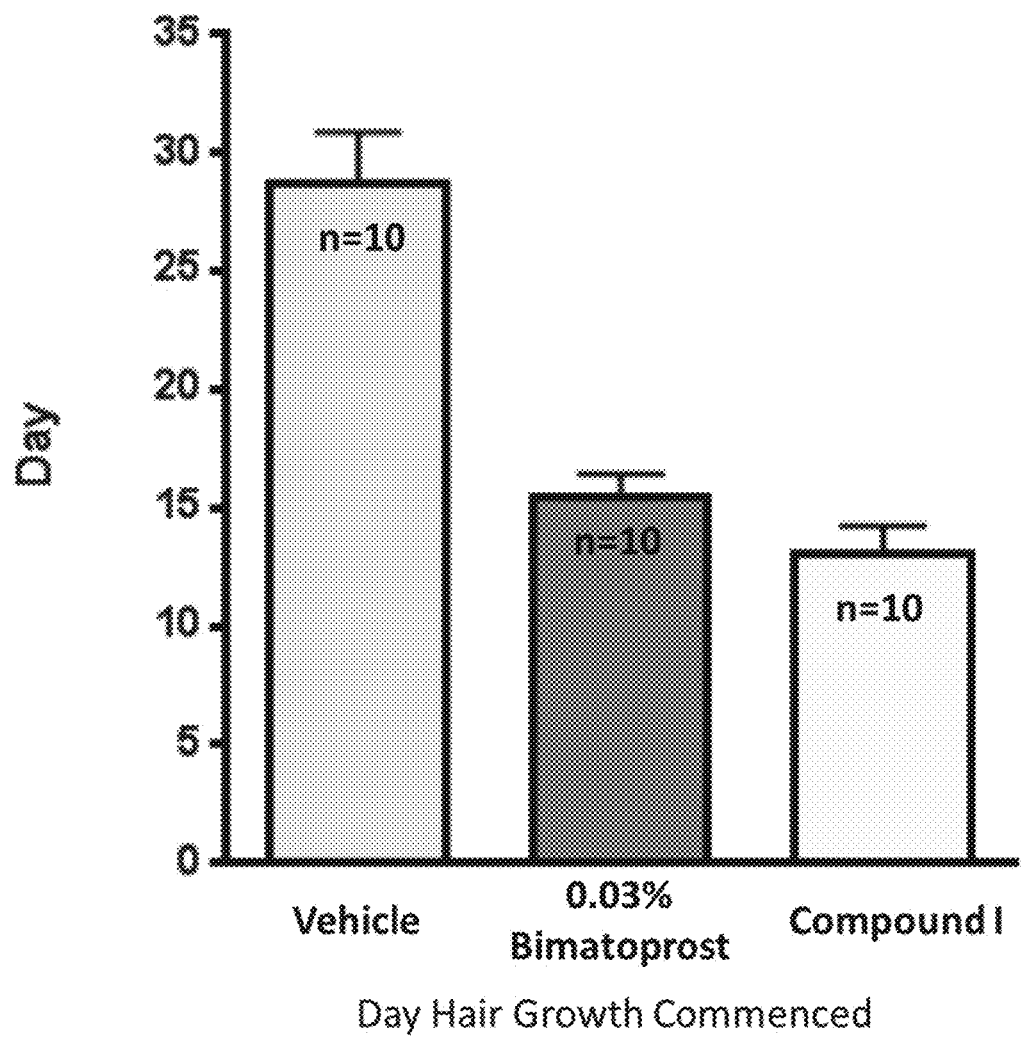
FIG. 4A and FIG. 4B show the results of an in vivo mouse hair re-growth model comparing the compound of Formula I to bimatoprost.
Figure 4B:
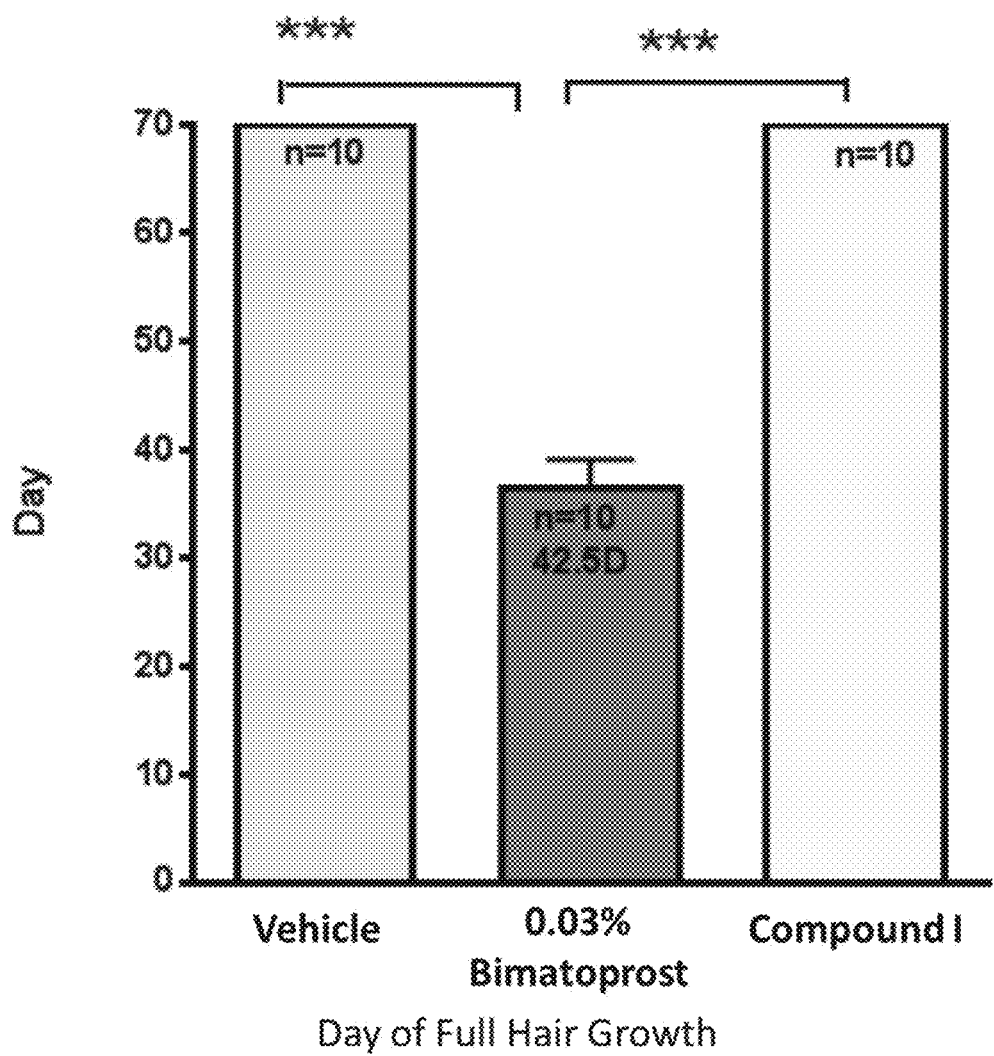

The results of this example can be seen FIGS. 4A and 4B. While Formula I appears to boost the start to hair re-growth it does not result in full hair re-growth. Administration of bimatoprost accelerates both time to start and full hair re-growth. This indicates that the compound of Formula I does not re-grow hair in this mouse model.

Example 3: Activity on Pre-Adipocytes

In this example it is shown that the compounds of Formulas I and II stimulates pre-adipocytes. In general, the compounds of Formulas I and II and bimatoprost were tested in the xCelligence impedance assay. Both bimatoprost and the compounds of Formulas I and II stimulate prostamide receptors on human pre-adipocytes.

More specifically, pre-adipocytes were purchased from Lonza. Cells were expanded in Pre-adipocyte maintenance medium (Lonza, Switzerland). Once expanded, 10,000 cells per well were plated into xCelligence 96-well plates and incubated at 37° C. for 72 hours until the impedance signal normalized. Once normalized, media was switched to serum-free pre-adipocyte media (PDM-2) for 2 hours at 37° C. Once the signal stabilized for 30 minutes, compounds were added at 7 concentrations ($10^{-5}$ to $10^{-9}$ M) and the signal measured for 20 minutes. The change in impedance was normalized to the background reading (buffer alone) and the $EC_{50}$ calculations were determined using prism software.

TABLE 1

| Compound | xCelligence $EC_{50}$ |
|---|---|
| Bimatoprost | $7.84 \times 10^{-7}$ |
| Formula I | $1.07 \times 10^{-8}$ |
| Formula II | $1.17 \times 10^{-8}$ |

The results in Table 1 show that formula I and II are relatively more potent than bimatoprost on human pre-adipocytes.

Figure 6:
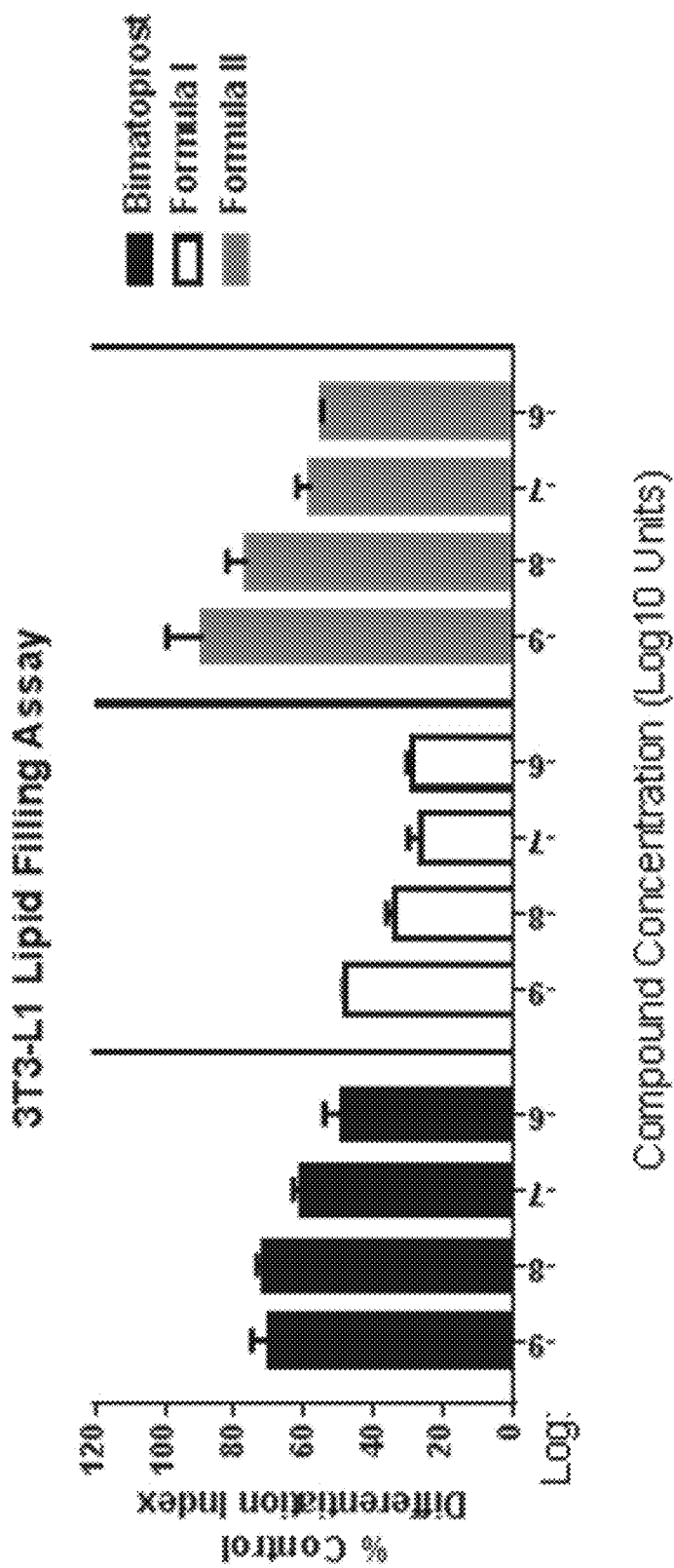
FIG. 6 shows the results of a pre-adipocyte cell differentiation assay in which 3T3-L1 mouse pre-adipocytes were induced to differentiate in the presence of bimatoprost, compounds of formula I and II for 3 days at the concentrations indicated.

In addition, 3T3-L1 mouse pre-adipocytes were induced to differentiate in the presence of bimatoprost, compounds of formula I and II for 3 days at the concentrations indicated. After 3 days the media and compounds were removed and replaced with adipocyte maintenance media. The media was change every 2 days following up to 8 days after initial induction. Lipid content was measured by using adipored dye (Lonza) and measured by fluorescent plate reader. The differentiation index was calculated as a ratio of differentiated wells to undifferentiated controls. 100% is defined as the differentiation index of differentiated control wells containing vehicle only. Differentiation media conditions were in DMEM/F-12 media containing insulin, isobutylmethylxanthine, and dexamethasone. Maintenance media contained insulin and dexamethasone only. The results are shown in FIG. 6.

Example 4: Reduction of Weight Gain and Lowering of Mean Body Weights

In this example it is shown that the compound of Formula I when administration orally daily results in reduction in weight gain and lower mean body weights. In general males rats (n=17-20) and female rats (n=17-20) were administered orally (by gavage) daily for 6 months at the doses indicated below. The compound of Formula I inhibited weight gain in both male and females at 5 mg/kg/day, and 0.3 mg/kg/day for females (p<0.05). The effect was somewhat reversible after administration of drug ceased.

More specifically, male and female rats (Hsd: Sprague Dawley) were assigned to four groups and administered test article formulations (0.03, 0.3, or 5 mg/kg/day compound of Formula I) or vehicle control article (0 mg/mL [0%] compound of Formula I [placebo] containing 3% hydroxypropyl-β-cyclodextrin [30 mg/mL (150 mg/kg/day)] and 10 mM phosphate buffered saline) via oral gavage once daily for 26 weeks at a volume of 5 mL/kg. Animals were sacrificed at the end of the dosing phase (up to 15 animals/sex/group) or at the end of the 4-week recovery phase (5 animals/sex/group in dose groups given vehicle control article and 5 mg/kg/day the compound of Formula I). These animals were on a restricted diet due to the length of the study. Weights were measured once per week.

Figure 5A:
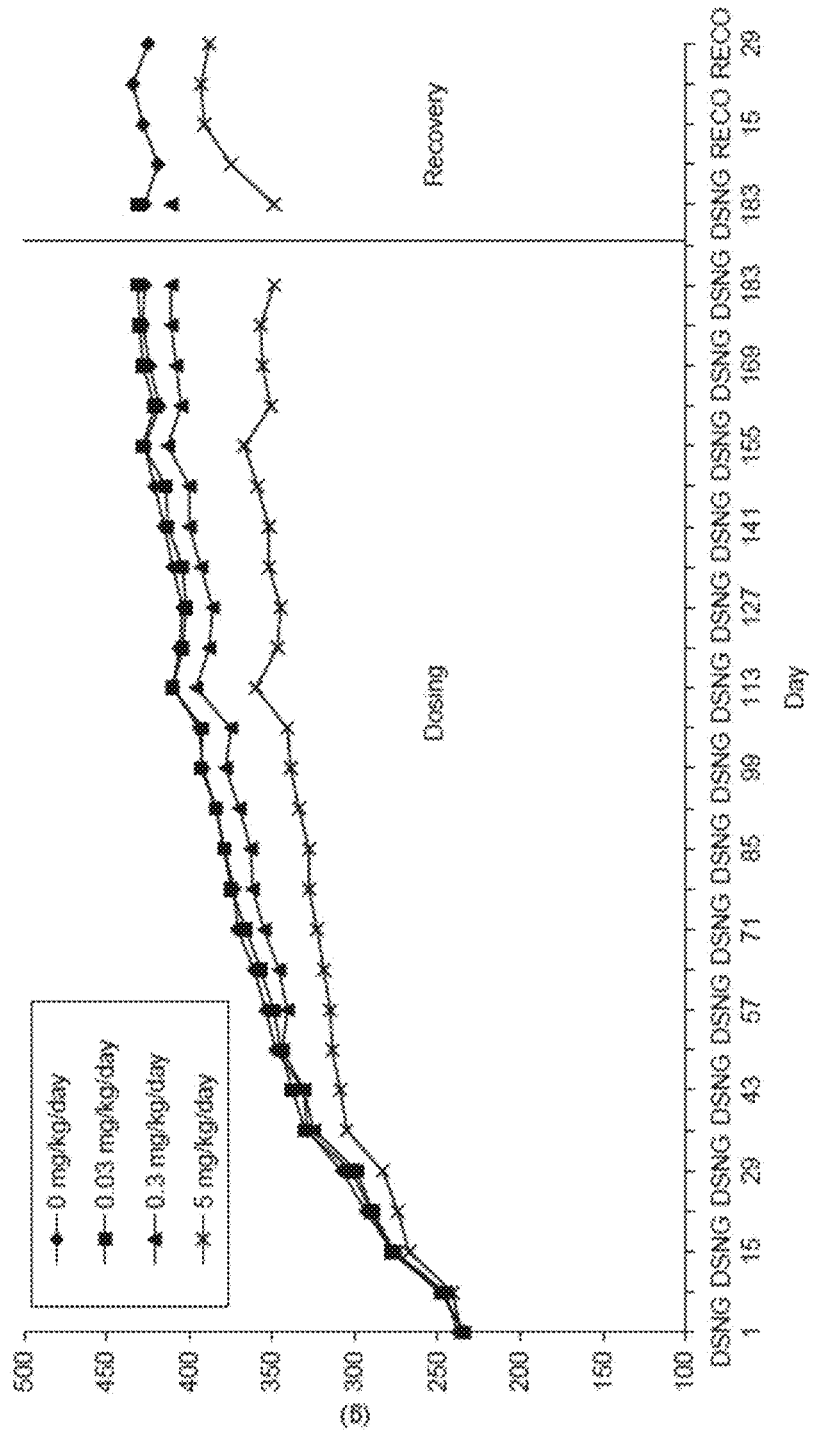
FIG. 5A and FIG. 5B show graphs of the weight change in rats upon oral administration of the compound of Formula I to rats.
Figure 5B:
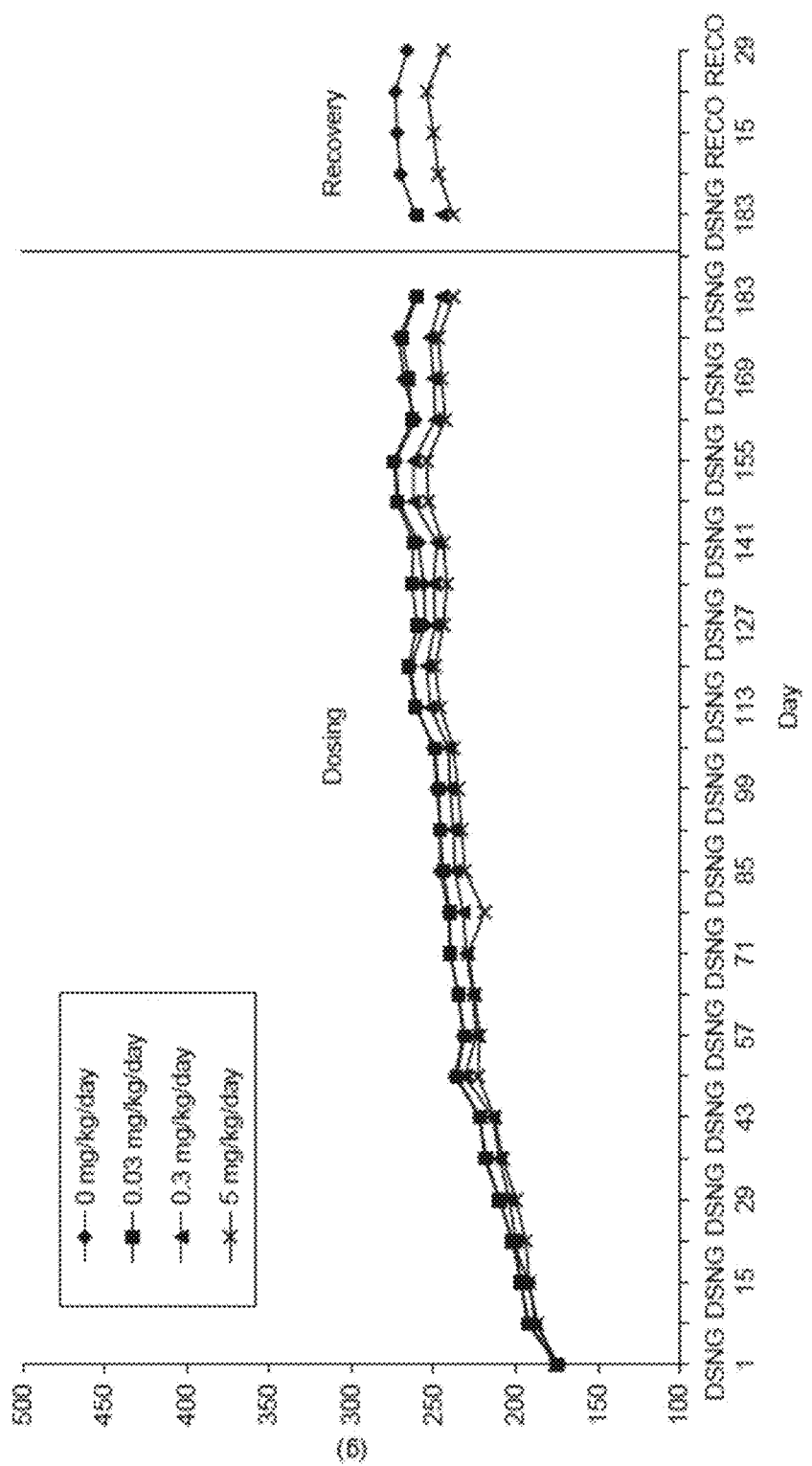

The results of the example are shown in FIGS. 5A (male rats) and 5B (female rats). As can be seen from the graphs, administration of Formula I daily resulted in a decrease in body weight gain starting at 14 days. This persistence in reduction continued throughout the treatment period, up to 183 days. Following the washout period, animals recovered a portion of the weight deficit they exhibited during the treatment period. This data indicates the weight loss is reversible. A skilled person will understand upon a reading of the present disclosure that dosages can be from about 0.05 mg/kg to about 5 mg/kg, and also from about 0.3 mg/kg to about 5 mg/kg.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated. To the extent that any recitations in the incorporated references conflict with any recitations herein, the recitations herein will control.

The foregoing descriptions details specific methods that can be employed to reduce fat, and in particular reduce fat without significant hair growth and/or additional hair growth, and represents the best mode contemplated. It should not be construed as limiting the overall scope hereof; rather, the ambit of the present disclosure is to be governed only by the lawful construction of the appended claims.

What is claimed is:

1. A method of reducing body fat in a subject comprising administering transdermally to a subject in need thereof an effective amount compound of Formula I, a compound of Formula II, or a mixture thereof:

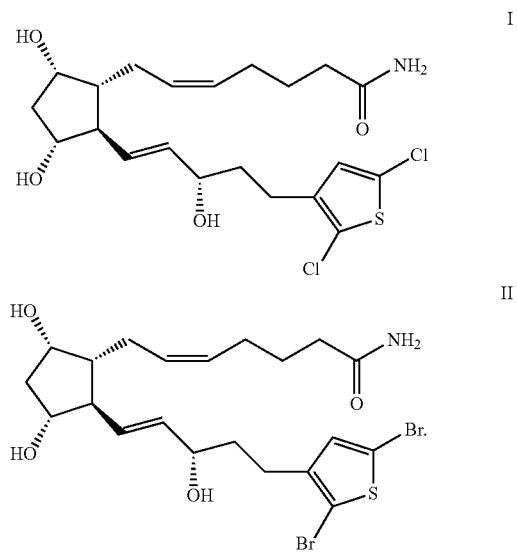

2. The method of claim 1, wherein an effective amount of the compound of formula I is administered.

3. The method of claim 1, wherein an effective amount of the compound of formula II is administered.

4. The method of claim 1, wherein the compound or mixture of compounds is administered in an amount effective for reducing fat without causing substantial hair growth at the site of fat reduction.

5. The method of claim 1, wherein the compound or mixture of compounds is administered in an amount effective for reducing fat without causing additional hair growth at the site of fat reduction.

6. The method of claim 1, wherein the compound or mixture of compounds is administered in an amount of about 0.05 mg/kg of body weight to about 5 mg/kg of body weight.

7. The method of claim 1, wherein the compound or mixture of compounds is administered in an amount of about 0.3 mg/kg of body weight to about 5 mg/kg of body weight.

8. The method of claim 1, wherein the compound or mixture of compounds is administered to at least one of the subject's submental region, thighs, abdomen, or waist.

9. The method of claim 1, wherein the compound or mixture of compounds is administered locally to a fat deposit.

* * * * *